(12) United States Patent
Millet

(10) Patent No.: US 11,793,778 B2
(45) Date of Patent: *Oct. 24, 2023

(54) COMPOSITIONS AND METHODS FOR KETO STACKING WITH BETA-HYDROXYBUTYRATE AND ACETOACETATE

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 247 days.

This patent is subject to a terminal disclaimer.

(21) Appl. No.: 17/157,000

(22) Filed: Jan. 25, 2021

(65) Prior Publication Data
US 2021/0137862 A1  May 13, 2021

Related U.S. Application Data

(63) Continuation of application No. 16/381,202, filed on Apr. 11, 2019, now Pat. No. 10,925,843.

(60) Provisional application No. 62/659,564, filed on Apr. 18, 2018.

(51) Int. Cl.
*A61K 31/19* (2006.01)
*A61K 31/121* (2006.01)

(52) U.S. Cl.
CPC ............ *A61K 31/19* (2013.01); *A61K 31/121* (2013.01); *A23V 2200/3322* (2013.01)

(58) Field of Classification Search
CPC .... A61K 31/121; A61K 31/132; A61K 31/19; A23V 2200/33; A23V 2200/3322
See application file for complete search history.

(56) References Cited

U.S. PATENT DOCUMENTS

| | | |
|---|---|---|
| 2,238,149 A | 4/1941 | Aeckerle |
| 2,976,073 A | 3/1961 | Russell et al. |
| 4,627,808 A | 12/1986 | Hughes |
| 4,771,074 A | 9/1988 | Lammerant et al. |
| 4,997,976 A | 3/1991 | Brunengraber et al. |
| 5,093,044 A | 3/1992 | Wretlind et al. |
| 5,100,677 A | 3/1992 | Veech |
| 5,116,868 A | 5/1992 | Chen et al. |
| 5,288,512 A | 2/1994 | Seiden |
| 5,292,774 A | 3/1994 | Hiraide et al. |
| 5,654,266 A | 8/1997 | Chen et al. |
| 5,700,670 A | 12/1997 | Yamagishi et al. |
| 6,207,856 B1 | 3/2001 | Veech |
| 6,217,915 B1 | 4/2001 | Uchansky et al. |
| 6,232,345 B1 | 5/2001 | Hiraide et al. |
| 6,316,038 B1 | 11/2001 | Veech |
| 6,323,237 B1 | 11/2001 | Veech |
| 6,380,244 B2 | 4/2002 | Martin et al. |
| 6,613,356 B1 | 9/2003 | Vlahakos |
| 6,706,756 B1 | 3/2004 | Fitzpatrick et al. |
| 6,835,750 B1 | 12/2004 | Henderson |
| 7,351,736 B2 | 4/2008 | Veech |
| 7,807,718 B2 | 10/2010 | Hashim et al. |
| 8,101,653 B2 | 1/2012 | Veech |
| 8,124,589 B2 | 2/2012 | Henderson |
| 8,426,468 B2 | 4/2013 | Henderson |
| 8,642,654 B2 | 2/2014 | Clarke et al. |
| 8,748,400 B2 | 6/2014 | Henderson |
| 9,138,420 B2 | 9/2015 | D'Agostino et al. |
| 9,211,275 B2 | 12/2015 | Clarke et al. |
| 9,675,577 B2 | 6/2017 | D'Agostino et al. |
| 9,717,767 B2 | 8/2017 | Carpenter et al. |
| 9,795,580 B2 | 10/2017 | Weeber et al. |
| 9,808,481 B2 | 11/2017 | Ritter et al. |
| 9,925,164 B1 | 3/2018 | Hashim |
| 9,957,246 B2 | 5/2018 | Stinchcomb et al. |
| 10,022,409 B2 | 7/2018 | Carpenter et al. |
| 10,051,880 B2 | 8/2018 | Clarke et al. |
| 10,245,242 B1 | 4/2019 | Millet |
| 10,245,243 B1 | 4/2019 | Millet |
| 10,292,592 B2 | 5/2019 | Marshall et al. |

(Continued)

FOREIGN PATENT DOCUMENTS

| CN | 86108978 A | 11/1987 |
|---|---|---|
| CN | 1256629 A | 6/2000 |

(Continued)

OTHER PUBLICATIONS

Acetoacetate, Acetone, and Dibenzylamine (A Contaminant in L-(+)-Beta-Hydroxybutyrate) Exhibit Direct Anticonvulsant Actions in Vivo, Epilepsia, Raven Press Ltd, New York, US, vol. 43, No. 4, Apr. 1, 2002 (Apr. 1, 2002), pp. 358-361.

Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1&keywords=ketone+pre+workout&qid=1597938465&sr=8-9.

Blazquez et al. Journal of Neurochemistry, 1999, vol. 72 No. 4, pp. 1759-1768. (Year: 1999).

(Continued)

*Primary Examiner* — Theodore R. Howell
(74) *Attorney, Agent, or Firm* — Workman Nydegger

(57) ABSTRACT

Compositions for delivering ketone bodies to a subject include one or more beta-hydroxybutyrate salts, one or more acetoacetate salts, beta-hydroxybutyric acid, and optionally acetoacetic acid. The compositions may optionally include one or more ketone body esters, such as one or more beta-hydroxybutyrate esters and/or one or more acetoacetate esters. An example composition contains about 2% to about 98% on a molar basis of the one or more beta-hydroxybutyrate salts and the one or more acetoacetate salts, about 2% to about 98% on a molar basis of the beta-hydroxybutyrate free acid and optionally the acetoacetate free acid, and optionally about 2% to about 98% on a molar basis of one or more ketone body esters.

20 Claims, 3 Drawing Sheets

(56) References Cited

U.S. PATENT DOCUMENTS

| | | | |
|---|---|---|---|
| 10,292,952 B2 | 5/2019 | Millet | |
| 10,512,615 B1 | 12/2019 | Millet | |
| 10,588,876 B2 | 3/2020 | Millet | |
| 10,588,877 B2 | 3/2020 | Arnold | |
| 10,596,128 B2 | 3/2020 | Millet | |
| 10,596,129 B2 | 3/2020 | Millet | |
| 10,596,130 B2 | 3/2020 | Millet | |
| 10,596,131 B2 | 3/2020 | Millet | |
| 10,660,958 B2 | 5/2020 | Clarke | |
| 10,736,861 B2 | 8/2020 | Millet | |
| 10,792,269 B2 | 10/2020 | Hashim | |
| 10,925,843 B2 | 2/2021 | Millet | |
| 10,973,786 B2 | 4/2021 | Millet | |
| 10,980,764 B1 | 4/2021 | D'Agostino et al. | |
| 10,980,772 B2 | 4/2021 | Millet | |
| 11,020,362 B2 | 6/2021 | Millet | |
| 11,033,553 B2 | 6/2021 | Millet | |
| 11,103,470 B2 | 8/2021 | Millet | |
| 11,185,518 B2 | 11/2021 | Millet | |
| 11,202,769 B2 | 12/2021 | Millet | |
| 2001/0014696 A1 | 8/2001 | Veech | |
| 2001/0041736 A1 | 11/2001 | Veech | |
| 2003/0022937 A1 | 1/2003 | Veech | |
| 2004/0138293 A1 | 7/2004 | Werner et al. | |
| 2004/0266872 A1 | 12/2004 | Veech | |
| 2005/0129783 A1 | 6/2005 | McCleary et al. | |
| 2006/0275253 A1 | 12/2006 | Ushida et al. | |
| 2007/0029913 A1 | 2/2007 | Chen | |
| 2007/0135376 A1 | 6/2007 | Henderson | |
| 2007/0179197 A1 | 8/2007 | Henderson | |
| 2008/0058416 A1 | 3/2008 | Greenwood et al. | |
| 2008/0287372 A1 | 11/2008 | Henderson | |
| 2009/0253781 A1 | 10/2009 | Veech | |
| 2010/0041751 A1 | 2/2010 | Henderson | |
| 2010/0056631 A1 | 3/2010 | Hisamura et al. | |
| 2010/0197758 A1 | 8/2010 | Andrews et al. | |
| 2010/0210726 A1 | 8/2010 | Kuriyama | |
| 2010/0298294 A1 | 11/2010 | Clarke et al. | |
| 2011/0237666 A1 | 9/2011 | Clarke et al. | |
| 2011/0287114 A1 | 11/2011 | Johnson | |
| 2012/0053240 A1 | 3/2012 | Rathmacher et al. | |
| 2012/0071548 A1 | 3/2012 | Veech | |
| 2012/0171165 A1 | 7/2012 | Buck et al. | |
| 2012/0202891 A1 | 8/2012 | Stinchcomb et al. | |
| 2013/0079406 A1 | 3/2013 | Veech | |
| 2013/0337116 A1 | 12/2013 | Petralia | |
| 2014/0256808 A1 | 9/2014 | Henderson | |
| 2014/0350105 A1 | 11/2014 | D'Agostino et al. | |
| 2015/0065571 A1 | 3/2015 | Clarke et al. | |
| 2015/0132280 A1 | 5/2015 | Lopez et al. | |
| 2015/0320809 A1 | 11/2015 | Carpenter et al. | |
| 2016/0193173 A1 | 7/2016 | Clarke et al. | |
| 2016/0256411 A1 | 9/2016 | Aung-Din | |
| 2017/0020844 A1 | 1/2017 | Galinski | |
| 2017/0029650 A1 | 2/2017 | Veling et al. | |
| 2017/0172969 A1 | 6/2017 | D'Agostino et al. | |
| 2017/0258745 A1 | 9/2017 | Millet | |
| 2017/0266148 A1 | 9/2017 | D'Agostino et al. | |
| 2017/0290792 A1 | 10/2017 | Cavaleri | |
| 2017/0296501 A1 | 10/2017 | Lowery et al. | |
| 2017/0298339 A1 | 10/2017 | Hanson et al. | |
| 2017/0304564 A1 | 10/2017 | Dehaan et al. | |
| 2018/0021274 A1 | 1/2018 | Arnold | |
| 2018/0021281 A1 | 1/2018 | Berger | |
| 2018/0055797 A1 | 3/2018 | Llosa et al. | |
| 2018/0057846 A1 | 3/2018 | Llosa et al. | |
| 2018/0195096 A1 | 7/2018 | Veech et al. | |
| 2018/0214399 A1 | 8/2018 | Spector et al. | |
| 2019/0099394 A1 | 4/2019 | Ari et al. | |
| 2019/0151267 A1 | 5/2019 | Millet | |
| 2019/0167613 A1 | 6/2019 | Millet | |
| 2019/0167614 A1 | 6/2019 | Millet | |
| 2019/0177673 A1 | 6/2019 | Llosa et al. | |
| 2019/0183220 A1 | 6/2019 | Takada | |
| 2019/0183820 A1 | 6/2019 | Millet | |
| 2019/0183821 A1 | 6/2019 | Millet | |
| 2019/0191755 A1 | 6/2019 | Garvey et al. | |
| 2019/0209501 A1 | 7/2019 | Tinsley et al. | |
| 2019/0262293 A1 | 8/2019 | Millet | |
| 2019/0313682 A1 | 10/2019 | Nagel | |
| 2019/0321309 A1 | 10/2019 | Millet | |
| 2020/0078973 A1 | 3/2020 | Valeze et al. | |
| 2020/0140371 A1 | 5/2020 | Verdin et al. | |
| 2020/0268701 A1 | 8/2020 | D'Agostino et al. | |

FOREIGN PATENT DOCUMENTS

| | | |
|---|---|---|
| CN | 1347319 A | 5/2002 |
| CN | 1972698 A | 5/2007 |
| CN | 101969769 A | 2/2011 |
| CN | 102164884 A | 8/2011 |
| CN | 104224823 A | 12/2014 |
| CN | 105050594 A | 11/2015 |
| CN | 106038532 A | 10/2016 |
| CN | 106459646 A | 2/2017 |
| CN | 106858066 A | 6/2017 |
| EP | 1827412 A1 | 9/2007 |
| EP | 1915144 A2 | 4/2008 |
| EP | 2283834 A2 | 2/2011 |
| EP | 2976073 A1 | 1/2016 |
| EP | 3094321 A1 | 11/2016 |
| FR | 2997302 A1 | 5/2014 |
| JP | 11-060434 A | 3/1999 |
| JP | 2002-521330 A | 7/2002 |
| JP | 2004-035417 A | 2/2004 |
| JP | 2015-042644 A | 3/2015 |
| JP | 2015-514104 A | 5/2015 |
| JP | 2016-514725 A | 5/2016 |
| JP | 2016-121128 A | 7/2016 |
| JP | 2017-046688 A | 3/2017 |
| JP | 2020-502652 A | 1/2020 |
| JP | 2020-527583 A | 9/2020 |
| JP | 2021-504476 A | 2/2021 |
| JP | 2021-506294 A | 2/2021 |
| RU | 2345546 C2 | 2/2009 |
| WO | 87/03808 A1 | 7/1987 |
| WO | 98/41200 A1 | 9/1998 |
| WO | 03/70823 A2 | 8/2003 |
| WO | 2005/107724 A1 | 11/2005 |
| WO | 2006/061624 A1 | 6/2006 |
| WO | 2007/115282 A2 | 10/2007 |
| WO | 2008/005818 A1 | 1/2008 |
| WO | 2008/021394 A2 | 2/2008 |
| WO | 2008/024408 A2 | 2/2008 |
| WO | 2009/089144 A1 | 7/2009 |
| WO | 2010/021766 A1 | 2/2010 |
| WO | 2011/101171 A1 | 8/2011 |
| WO | 2013/150153 A1 | 10/2013 |
| WO | 2014/153416 A1 | 9/2014 |
| WO | 2015/071811 A1 | 5/2015 |
| WO | 2015/156865 A1 | 10/2015 |
| WO | 2016/123229 A1 | 8/2016 |
| WO | 2016/149687 A1 | 9/2016 |
| WO | 20171156446 A1 | 9/2017 |
| WO | 20171165443 A1 | 9/2017 |
| WO | 20171165445 A1 | 9/2017 |
| WO | 2017/208217 A2 | 12/2017 |
| WO | 20181055388 A1 | 3/2018 |
| WO | 2018/089863 A1 | 5/2018 |
| WO | 2018/114309 A1 | 6/2018 |
| WO | 2018/175879 A1 | 9/2018 |
| WO | 2018/187324 A1 | 10/2018 |
| WO | 2019/018683 A1 | 1/2019 |
| WO | 20191204148 A1 | 10/2019 |
| WO | 2019/237152 A1 | 12/2019 |

OTHER PUBLICATIONS

Craciun, S. et al. Microbial conversion of choline to trimethylamine requires a glycyl radical enzyme, 2012, PNAS, 109(52): 21307-21312 (Year: 2012).

Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).

(56) References Cited

OTHER PUBLICATIONS

Extended European Search Report received for EP Patent Application No. 19788264.0, dated Dec. 20, 2021, 11 pages.
Haces M L et al: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.
Ichim, T. et al., Experimental support for the effects of a probiotic/digestive enzyme supplement on serum cholesterol concentrations and the intestinal microbiome, 2016, Journal of Translational Medicine, 14(184), 1-9 (Year: 2016).
International Preliminary Report on Patentability received for PCT Patent Application No. PCT/US2020/016952, dated Aug. 26, 2021, 7 pages.
International Preliminary Report on Patentability received for PCT Patent Application No. PCT/US20/37289, dated Dec. 30, 2021, 6 pages.
International Preliminary Report on Patentability received for PCT Patent Application No. PCT/US2019/048364, dated Mar. 11, 2021, 7 pages.
International Preliminary Report on Patentability received for PCT Patent Application No. PCT/US2020/017552, dated Aug. 26, 2021, 7 pages.
International Preliminary Report on Patentability received for PCT Patent Application No. PCT/US2020/017555, dated Aug. 26, 2021, 7 pages.
International Preliminary Report on Patentability received for PCT Patent Application No. PCT/US2020/017556, dated Aug. 26, 2021, 7 pages.
International Preliminary Report on Patentability received for PCT Patent Application No. PCT/US2020/033159, dated Nov. 25, 2021, 6 pages.
International Search Report and Written Opinion received for PCT Patent Application No. PCT/US20/017555, dated May 4, 2020, 8 pages.
International Search Report and Written Opinion received for PCT Patent Application No. PCT/US21/045186, dated Nov. 22, 2021, 10 pages.
International Search Report and Written Opinion received for PCT Patent Application No. PCT/US21/17078, dated Apr. 23, 2021, 9 pages.
Kim Do Young et al., "Ketone bodies are protective against oxidative stress in neocortical neurons," Journal of Neurochemistry, vol. 101, Issue 5, Jun. 1, 2007, pp. 1316-1326.
Maalouf Met al., "Ketones inhibit mitochondrial production of reactive oxygen species production following glutamate excitotoxicity by increasing NADH oxidation," Neuroscience, New York, NY, US, vol. 145, Issue 1, Mar. 2, 2007, pp. 256-264.
Maalouf Met al., "The neuroprotective properties of calorie restriction, the ketogenic diet, and ketone bodies," Brain Research Reviews, Elsevier, NL, vol. 59, No. 2, Mar. 1, 2009, pp. 293-315.
Malo, M. S. et al., Intestinal alkaline phosphatase preserves the normal homeostasis of gut microbiota, 2010, Gut, 59, 1476-1484 (Year: 2010).
Pete J Cox et al., "Acute nutritional ketosis: implications for exercise performance and metabolism," Extreme Physiology & Medicine, vol. 3, Issue 1, Dec. 1, 2014, pp. 1-9.
Robson et al. Expert Opin. Drug Saf. (2011), vol. 10, pp. 675-685 (Year: 2011).
Stubbs et al., "On the Metabolism of Exogenous Ketones in Humans", frontiers in Physiology, vol. 8, 2017, 13 pages.
Tsai et al., "Stereoselective effects of 3-hydroxybutyrate on glucose utilization of rat cardiomyocytes" life Sciences 78(2006) pp. 1385-1391.
A New Toy Measuring Blood Ketones. Diet Doctor, Aug. 21, 2012. Dowaloded Apr. 1, 2015. http://www.dietdoctor.com/a-new-toy-measuring-blood-ketoones.
A New Toy Measuring Blood Ketones. Diet Doctor, Aug. 21, 2012. Downloaded Apr. 1, 2015. http://www.dietdoctor.com/a-new-toy-measuring-blood-ketoones.

Arendash et al. "Caffeine and Coffee as Therapeutics Against Alzheimer's Disease", Journal of Alzheimer's Disease 20, 2010, S117-S126.
Arnold, Instant Ketosis?, (2013), Aug. 4, 2013 (retrieved on Apr. 21, 2017), p. 1-3. Retrieved from the internet; URL: < http://patrickarnoldblog.com/instant-ketosis/. (Year: 2013).
Bastin et al., "Salt Slection and Optimisation Procedures for Pharmaceutical New Chemical Entities", American Chemical Society and The Royal Society of Chemistry, vol. 4, No. 5, 2000, pp. 427-435.
Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.
Dietary Guidelines Recommendations at https://health.gov/our-work/food-nutrition/2015-2020-dietary-guidelines/guidelines/ appendix-7/ (2010) (retrieved from the internet Oct. 20, 2020) (Year: 2010).
Dolson, Laura. How to Test Your Blood for Ketones. Downloaded Apr. 1, 2015. http://lowcarbdiets.about.com/od/KetogenicDiets/a/How-to-Test-Blood-For-Ketones.htm.
Dolson, Laura. How to Test Your Blood for Ketones. Downloaded Apr. 1, 2015. http://lowcarbdiets.about.eom/od/KetogenicDiets/a/How-to-Test-Blood-For-Ketones.htm.
Extended European Search Report issued in PCT/US2017021886 dated Oct. 17, 2019.
First Examination Report for New Zealand Patent Application No. 711433 issued by the New Zealand Intellectual Property Office dated Mar. 10, 2016.
First Office Action issued by the Chinese State Intellectual Property Office dated Nov. 4, 2016 for corresponding Chinese Patent Application No. 201480016818.0.
Hashim, Sami A., et al., "Ketone body therapy: from the ketogenic diet to the oral administration of ketone ester", Journal of Lipid Research, vol. 55, 2014.
Hashim, Sarni A., et al., "Ketone body therapy: from the ketogenic diet to the oral administration of ketone ester", Journal of Lipid Research, vol. 55, 2014.
Haywood A, Glass BD. Pharmaceutical excipient—where do we begin? Australian Prescriber. 2011; 34: 112-114.
Haywood A, Glass BD. Pharmaceutical excipients—where do we begin? Australian Prescriber. 2011; 34: 112-114.
Henderson, Samuel T. "Ketone Bodies as a Therapeutic for Alzheimer's Disease." Neurotherapeutics. Jul. 2008;5(3):470-80.
Holtzman et al., "Role of adenosine receptors in caffeine tolerance", J. Pharmacol. Exp. Ther., 1991 ;256(1 ):62-68.
International Search Report and Written Opinion issued in PCT/US19/48357 dated Nov. 18, 2019.
International Search Report and Written Opinion issued in PCT/US19/48364 dated Nov. 15, 2019.
International Search Report and Written Opinion issued in PCT/US20/16952 dated Apr. 22, 2020.
International Search Report and Written Opinion issued in PCT/US20/17552 dated May 4, 2020.
International Search Report and Written Opinion issued in PCT/US20/17555 dated May 4, 2020.
International Search Report and Written Opinion issued in PCT/US20/17556 dated May 4, 2020.
International Search Report and Written Opinion received for PCT Patent Application No. PCT/US20/37289, dated Sep. 30, 2020, 8 pages.
International Search Report and Written Opinion received for PCT Patent Application No. PCT/US2020/033159, dated Aug. 12, 2020, 9 pages.
International Search Report cited in PCT/US18/62093 dated Feb. 1, 2019.
International Search Report cited in PCT/US19/27214 dated Jun. 25, 2019.
International Search Report in PCT/US18/62096 dated Feb. 11, 2019.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.

(56) References Cited

OTHER PUBLICATIONS

James, "Optical Purity and Enantiomeric Excess" at https://www.masterorganicchemistry.com/2017/02/24/optical-purity-and-enantiomeric-excess/. (Retrieved from the internet Nov. 6, 2018) (Year: 2018).
Karppanen et al., J. Human Hypertension (2005), vol. 19, pp. S10-S19. (Year: 2005).
Karppanen, H., et al., "Why and how to implement sodium, potassium, calcium, and magnesium changes in food items and diets?"
Kesl, et al., "Effects of exogenous ketone supplementation on blood ketone, glucose, triglyceride, and lipoprotein levels in Sprague-Dawley rats", Nutrition & Metabolism (2016).
Kesl, et al., "Effects of exogenous ketone supplementation on blood ketone, glucose, triglyceride, and lipoprotein levels in Spraque-Dawley rats", Nutrition & Metabolism (2016).
Kirsch, Jr et al. "Butanediol Induced Ketosis Increases Tolerance to Hypoxia in the Mouse." Stroke. 1980, vol. 11, No. 3, pp. 506-513.
Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.
Krotkiewski, "Value of VLCD Supplementation with Medium Chain Triglycerides", Int J Obes Relat Metab Disord, Sep. 2001, 25(9), pp. 1393-1400.
Murray, Andrew J., et al. "Novel ketone diet enhances physical and cognitive performance", The FASEB Journal, Vo. Dec. 30, 2016.
Non-Final Office Action received for U.S. Appl. No. 16/381,202, dated Aug. 11, 2020, 8 pages.
Non-Final Office Action received for U.S. Appl. No. 16/720,211, dated Oct. 28, 2020, 14 pages.
Non-Final Rejection dated Sep. 9, 2020 for U.S. Appl. No. 16/783,956.
Notice of Allowance received for U.S. Appl. No. 15/454,157, dated Feb. 26, 2019.
Notice of Allowance received for U.S. Appl. No. 16/224,408, dated Nov. 27, 2019.
Notice of Allowance received for U.S. Appl. No. 16/224,485, dated Nov. 27, 2019.
Notice of Allowance received for U.S. Appl. No. 16/272,359, dated Feb. 11, 2019.
Notice of Allowance received for U.S. Appl. No. 16/381,202, dated Nov. 10, 2020, 8 pages.
European Search Report received for EP Patent Application No. 20755289A, dated Oct. 11, 2022, 7 pages.
European Search Report received for EP Patent Application No. 20755994.9, dated Sep. 21, 2022, 6 pages.
European Search Report received for EP Patent Application No. 20805593.9, dated Dec. 16, 2022, 9 pages.
Extended European Search Report received for EP Patent Application No. 20755770.3, dated Sep. 1, 2022, 7 pages.
International Preliminary Report on Patentability received for PCT Patent Application No. PCT/US20211017078, dated Aug. 18, 2022, 7 pages.
John C Newman et al: "beta-Hydroxybutyrate: A Signaling Metabolite", Annual Review of Nutrition, vol. 37, Aug. 21, 2017 (Aug. 21, 2017), pp. 51-76, XP055771586.
Lile et al. Drug Alcohol Depend. 2012, 122 (1-2), 61-69.
Maguire et al., "Gut dysbiosis, leaky gut, and intestinal epithelial proliferation in neurological disorders: towards the development of a new therapeutic using amino acids, prebiotics, probiotics, and postbiotics", Rev Neurosci . Jan. 28, 2019, vol. 30, No. 2, pp. 179-201.
National Center for Biotechnology Information. PubChem Compound Summary for CID 441, 3-Hydroxybutyric acid, https://pubchem.ncbi.nlm.nih.gov/compound/3-Hydroxybutyric-acid. (Year: 2005).
Rich A.J., "Ketone Bodies as Substrates," Proceedings of the Nutrition Society (1990), vol. 49, 361-373.
Slavin, J. Fiber and Prebiotics: Mechanisms and Health Benefits, 2013, Nutrients, 5: 1417-1425 (Year: 2013).

The Medical Republic, 2018, Sustained Release Sodium Butyrate Supplement Now Available to Support Management of GI Disorders, https://medicalrepubliccom.au/sustained-release-sodium-butyrate-supplement-now-available-support-management-gi-disorders/15791; newly cited (Year: 2018).
Wu et al., "Medium-Chain Triglycerides in Infant Formulas and Their Relation to Plasma Ketone Body Concentrations," Pediatric Research, vol. 20, No. 4, (1986), pp. 338-341.
Yang Y. et al., Role of Adherent-Invasive *Escherichia coli* in Inflammatory Bowl Disease, Letters in Biotechnology, No. 06, Nov. 30, 2016.
Zaleski, A. et al., Butyric acid in irritable bowel syndrome, 2013, Prz Gastroenterol, 8(6), 350-353 (Year: 2013).
Grootaert, C. Comparison of prebiotic effects of arabinoxylan oligosaccharides and inulin in a simulator of the human intestinal microbial ecosystem, 2009, FEMS Microbiology Ecology, 69: 231-242 (Year: 2009).
Holscher, H. Dietary fiber and prebiotics and the gastrointestinal microbiota, 2017, Gut Microbes, 8(2): 172-184 (Year: 2017).
International Search Report and Written Opinion received for PCT Patent Application No. PCT/US2021/063559, dated Mar. 18, 2022, 9 pages.
Sanchez, J. I. et al. Arabinoxylan-oligosaccharides (AXOS) affect the protein/carbohydrate fermentation balance and microbial population dynamics of the Simulator of Human Intestinal Microbial Ecosystem, 2009, Microbial Biotechnology, 2(1): 101-113 (Year: 2009).
Walton, G. et al. A randomised, double-blind, placebo controlled cross-over study to determine the gastrointestinal effects of consumption of arabinoxylan-oligosaccharides enriched bread in healthy volunteers, 2012, Nutrition Journal, 11(36): 1-11 (Year: 2012).
Notice of Allowance received for U.S. Appl. No. 16/409,501, dated Jan. 14, 2020.
Notice of Allowance received for U.S. Appl. No. 15/936,849, dated Jan. 24, 2019.
Notice of Allowance received for U.S. Appl. No. 16/272,359, dated Aug. 7, 2019.
Nova Max Plus Glucose and Ketone Testing with One Monitor. Downloaded Apr. 1, 2015. http://www.novacares.com/nova-max-plus/.
Office Action cited in U.S. Appl. No. 16/720,211 dated Oct. 28, 2020.
Office Action cited in U.S. Appl. No. 16/996,509 dated Oct. 26, 2020.
Office Action received for U.S. Appl. No. 14/455,385, dated Jan. 2, 2015.
Office Action received for U.S. Appl. No. 14/860,092, dated Mar. 9, 2016.
Office Action received for U.S. Appl. No. 14/860,092, dated Oct. 17, 2016.
Office Action received for U.S. Appl. No. 15/454,157, dated Jan. 11, 2018.
Office Action received for U.S. Appl. No. 15/454,157, dated Jun. 13, 2018.
Office Action received for U.S. Appl. No. 15/610,668, dated Jul. 25, 2018.
Office Action received for U.S. Appl. No. 15/936,820, dated Nov. 14, 2018.
Office Action received for U.S. Appl. No. 15/936,849, dated Nov. 14, 2018.
Office Action received for U.S. Appl. No. 16/272,145 dated Jan. 10, 2020.
Office Action received for U.S. Appl. No. 16/381,202, dated Oct. 22, 2019.
Parker, Steve, "Ketogenic Mediterraanean Diet: Version 2.3," Nov. 23, 2010, pp. 1-3. (Year: 2010).
Parker, Steve, "Ketogenic Mediterranean Diet: Version 2.3," Nov. 23, 2010, pp. 1-3. (Year: 2010).
PCT International Search Report and Written Opinion cited in PCT/US2014/031237 dated Jul. 15, 2014.
PCT International Search Report and Written Opinion issued by the International Searching Authority dated Jul. 15, 2014 or International Patent Application No. PCT/US2014/031237.

(56) References Cited

OTHER PUBLICATIONS

Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.
Pubchem, "Acetoacetic acid" Electronic Resource: https://pubchem.ncbi.nlm.nih.gov/compound/Acetoacetic-acid, Retrieved on Sep. 3, 2019.
Requirement for Restriction/Election received for U.S. Appl. No. 16/551,570, dated Sep. 28, 2020, 6 pages.
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Sajewicz et al. in Journal of Liquid Chromatography & Related Technologies, 33:1047-1057 (2010) (Year: 2010).
Serum Ketones Test. MedlinePlus Medical Encyclopedia. Downloaded Apr. 1, 2015. http://www.nlm.nih.gov/medlineplus/ency/article/003498.htm.
Shigeno etal. in Biosci. Biotech. Biochem., 56(2), 320-323 (1992) (Year: 1992).
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
Tisdale, "Reduction of weight loss and tumour size in a cachexia model by a high fat diet", British Journal of Cancer, Jul. 1987, vol. 56, p. 39-43.
Vandenberghe et al. in Can. J. Physiol. Pharmacol. 95: 455-458 (2017) (Published at www.nrcresearchpress.com/cjpp on Nov. 25, 2016). (Year: 2016).
Veech, "The Therapeutic Implications of Ketone Bodies: The Effects of Ketone Bodies in Pathological Conditions: Ketosis, Ketogenic Diet, Redox States, Insulin Resistance, and Mitochondrial Metabolism", Prostaglandins Leukot Essent Fatty Acids, Mar. 2004, 70(3), pp. 309-319.
Veech, et al., "Ketone Bodies Mimic the Life Span Extending Properties of Caloric Restriction", IUBMB Life Feb. 8, 2017.
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004,70(3):309-19.
Vorgerd, M. And J. Zange. Treatment of glycogenosys type V (McArdle disease) with creatine and ketogenic diet with clinical scores and with 31P-MRS on working leg muscle. Acta Myologica, 2007; XXVI; pp. 61-63.

Anonymous: "Blue Lemon Ice Advanced Formula", Mintel, Database accession No. 4315637, 2016, pp. 3.
Anonymous: "Strawberry Pineapple Flavour Pre-Exertion Performance Optimizer", Mintel, Database accession No. 5661617, 2018, pp. 4.
Budin. N. et al., "Efficient synthesis of the ketone body ester (R)-3-hydroxybutyryl-(R)-3-hydroxybutyrate and its (S, S) enantiomer," Bioorganic Chemistry, vol. 80, Oct. 2018, pp. 560-564.
Huang Dexiang, "Clinical Parenteral nutrition", Jan. 31, 1994, pp. 1-20.
International Preliminary Report on Patentability received for PCT Patent Application No. PCT/US2018/062093, dated Jun. 4, 2020, 6 pages.
International Preliminary Report on Patentability received for PCT Patent Application No. PCT/US2021/045186, dated Mar. 9, 2023, 7 pages.
International Preliminary Report on Patentability received for PCT Patent Application No. PCT/US2021/050302, dated Mar. 2, 2023, 8 pages.
Kaster M.P. et al, "Caffeine acts through neuronal adenosine A2A receptors to prevent mood and memory dysfunction triggered by chronic stress", Proceedings of the National Academy of Sciences, vol. 112, No. 25, Jun. 8, 2015, pp. 7833-7838.
Lonza, Duocap Capsules, Feb. 16, 2018, https://web.archive.org/web/20180216001656/https://www.capsugel.com/consumer-health-nutrition-products/duocap-capsules (Year: 2018).
Luis Villasenor, "Supplements and Ketogenic Diets—Facts and Myths", Retrieved from https://www.ketogains.com/2015/09/supplements-and-ketogenic-diets-facts-and-myths/, Sep. 18, 2015, pp. 15.
Lytra. G. et al., "Distribution and Organoleptic Impact of Ethyl 3-Hydroxybutanoate Enantiomers in Wine," J. Agric. Food Chem, vol. 63, Issue 48, 2015, pp. 10484-10491.
Mangels D.R. et al, "Catechins as Potential Mediators of Cardiovascular Health", Translational Sciences, vol. 37, No. 5, May 1, 2017, pp. 757-763.
Sorensen et al. ("Simultaneous determination of ß-hydroxybutyrate and ß-hydroxy-ß-methylbutyrate in human whole blood using hydrophilic interaction liquid chromatography electrospray tandem mass spectrometry", Clinical Biochemistry, 2013, vol. 46, pp. 1877-1883) (Year: 2013).
Bala et al. Drug Invention Today. Jun. 1, 2018;10(6), 929-931.
O'Meara, Cyndi, Changing Habits, Ketosis—Can we achieve it in a pill?, https://changinghabits.com.au/ketosis-can-we-achieve-it-in-a-pill/, 12 pages, (Jan. 13, 2017).
Sara, How do you know which product is right for you? How to choose exogenous ketones, https://ketosupplements.co.uk/how-to-choose-exogenous-ketones/, 10 pages, (Sep. 25, 2017).
Short, Jay, Effects of A Ketone/Caffeine Supplement On Cycling and Cognitive Performance, Master's thesis, Ohio State University, 61 pages, (Jan. 1, 2017).

COMPOSITIONS AND METHODS FOR KETO STACKING WITH BETA-HYDROXYBUTYRATE AND ACETOACETATE

CROSS-REFERENCE TO RELATED APPLICATIONS

This Application is a continuation of U.S. patent application Ser. No. 16/381,202, filed Apr. 11, 2019, now U.S. Pat. No. 10,925,843, which claims the benefit of U.S. Provisional Patent Application No. 62/659,564, filed Apr. 18, 2018, which are incorporated herein by reference in their entirety.

BACKGROUND

1. Field of the Invention

Disclosed herein are compositions including effective ratios of beta-hydroxybutyrate and acetoacetate, stacked compositions including two or more different forms of ketone bodies, and methods of using the same for producing elevated blood levels of ketone bodies in a mammal.

2. Related Technology

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation of ketone bodies for energy ("ketosis"). Ketone bodies can be used by cells of the body as a fuel to satisfy the body's energy needs, including the brain and heart. During prolonged fasting, for example, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is referred to as ketosis. Between 1.0 mmol/L and 3.0 mmol/L the condition is called "nutritional ketosis."

Upon transitioning into ketosis, or in other words, during ketogenic metabolism in the liver, the body uses dietary and bodily fats as a primary energy source. Consequently, once in ketosis, one can induce loss of body fat by controlling dietary fat intake and maintaining low carbohydrate to sustain ketosis.

While in ketosis, the body is in ketogenesis and is essentially burning fat for its primary fuel. The body cleaves fats into fatty acids and glycerol and transforms fatty acids into acetyl CoA molecules, which are then eventually transformed through ketogenesis into the water-soluble ketone bodies beta-hydroxybutyrate ("β-hydroxybutyrate" or "beta-hydroxybutyrate"), acetoacetate, and acetone in the liver. beta-hydroxybutyrate and acetoacetate are the ketone bodies used by the body for energy while acetone is removed as a by-product of ketogenesis.

The metabolism of ketone bodies is associated with several beneficial effects, including anticonvulsant effects, enhanced metabolism by the brain, neuroprotection, muscle sparing properties, and improved cognitive and physical performance. Science-based improvements in efficiency of cellular metabolism, managed through ketone supplementation, can have beneficial impacts on physical, cognitive health, and psychological health, and a long-term impact on health with respect to the common avoidable diseases such as obesity, cardiovascular disease, neurodegenerative diseases, diabetes, and cancer.

Despite the many health advantages of pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to enter ketosis is by depleting glucose stores in the body through fasting combined with exercise. This, however, is physically and emotionally demanding and can be extremely challenging even for the most motivated and disciplined.

Additionally, the transition into ketosis is often accompanied by hypoglycemia, which can cause lethargy and light-headedness in many, resulting in an uncomfortable physiological and mental state commonly referred to as "low-carb flu." In addition, many people experience down regulation in their metabolism as the body goes into "energy-saving" mode. Some suggest that these transitory symptoms may last as long as two to three weeks. During this transition period, if any meal or snack containing carbohydrates over a restricted amount is consumed, there is an immediate termination of ketogenesis, exiting the body from a state of ketosis, as the body shifts back to glucose as its primary fuel, and the transition into ketosis must begin anew.

If a subject is successful in establishing ketosis, the act of sustaining ketosis is likewise difficult, if not more difficult, due to the need to maintain a rigid dietary ratio of carbohydrates and protein to fats.

To overcome the difficulties associated with inducing ketosis via fasting and exercise, methods of inducing ketosis through direct administration of ketone bodies have been proposed. While some of these may work to induce ketosis in an individual, several limitations remain. In particular, while relatively brief spikes in blood ketone body levels may be achieved, such spikes tend to wane much faster than desired. Accordingly, there is a long felt and continuing need for compositions and methods capable of promoting and maintaining ketosis over long periods of time.

BRIEF SUMMARY

Disclosed herein are compositions and methods for promoting and maintaining ketosis. Exogenous ketone bodies (i.e., beta-hydroxybutyrate and acetoacetate) may be provided in three general forms: 1) salt forms, 2) ester forms, and 3) free acid forms (i.e., beta-hydroxybutyric acid and/or acetoacetic acid). Each of these forms provides certain benefits but can have undesirable side effects.

The compositions described herein may be provided as a "stacked" mixture combining at least two of these forms. Such stacked compositions can beneficially limit the occurrence and/or severity of undesirable side-effects and/or can permit administration of higher doses of exogenous ketone bodies. Stacked compositions therefore permit delivery of substantially higher amounts of exogenous ketone bodies while reducing or minimizing detrimental effects of delivering too much of one type of exogenous ketone body.

Moreover, a stacked composition can provide higher and/or more sustained levels of ketone bodies in the blood as compared to an otherwise similar amount provided in a single form. For example, a stacked formulation can be tailored to provide a more preferable or more optimized release profile, such as one that combines the benefits of more rapid onset with the benefits of a more extended release, and/or one that provides an overall greater pharmacokinetic area under the curve (AUC). Stacked compositions therefore provide for timed delivery or availability of ketone bodies, which provides for more even blood concentration of ketone bodies and a significantly longer delivery "tail" of exogenous ketone bodies, such as 1-8 hours after consuming the stacked composition.

Stacked compositions permit the selection and tailoring of different ratios and combinations of various forms of beta-hydroxybutyrate and acetoacetate to address different nutritional and/or health needs of different individuals or groups. For example, different ratios and/or combinations of different types of exogenous ketone bodies can be selected to address different conditions based on a person's age, gender, state of health, disease condition, and the like.

Embodiments disclosed herein are directed to ketogenic compositions formulated for inducing and sustaining ketosis in a subject. An example composition includes a mixture of beta-hydroxybutyrate and acetoacetate, wherein the beta-hydroxybutyrate is included in an amount of about 55% to about 95% of the mixture and the acetoacetate is included in an amount of about 5% to about 45% of the mixture. The beta-hydroxybutyrate/acetoacetate mixture may be combined with a dietetically or pharmaceutically acceptable carrier.

As explained in more detail below, exogenous acetoacetate can be utilized for energy during ketolysis with less reduction in the subject's available $NAD^+$ as compared to exogenous beta-hydroxybutyrate. Certain compositions described herein are therefore formulated to include proportionally sufficient acetoacetate to limit the undesirable reduction in available $NAD^+$ as compared to a similar dose of beta-hydroxybutyrate only or a similar dose of beta-hydroxybutyrate with insufficient acetoacetate.

At the same time, however, too much acetoacetate relative to beta-hydroxybutyrate can lead to other undesirable side effects. Excessive acetoacetate is associated with high levels of acetone in the blood. Much of this acetone is expelled from the subject's body through the breath, resulting in the telltale and often unpleasant "keto breath" associated with a subject in ketosis.

Disclosed compositions are beneficially formulated to balance the different benefits and limitations of beta-hydroxybutyrate and acetoacetate by including proportions of each that effectively promote and/or sustain ketosis, comparatively limit the reduction in available $NAD^+$ in the subject, and limit excess levels of acetone in the blood. Regulating the amount of each separate ketone body component and/or providing different stacked forms of exogenous ketone bodies beneficially allows for tailored compositions optimized for particular application needs or preferences.

Ketogenic compositions described herein may be useful as one or more of: weight loss supplement; treatment for high blood glucose or type II diabetes; brain tonic; athletic performance enhancer; preventative against metabolic dysfunction, mitochondrial defect, and/or insulin resistance; adjunct to a ketogenic diet; anti-aging supplement; and other uses associated with improved metabolic health.

In one embodiment, a ketogenic composition includes at least two separate exogenous ketone bodies selected from the group consisting of: (i) a beta-hydroxybutyrate salt; (ii) an acetoacetate salt; (iii) a beta-hydroxybutyrate ester; (iv) an acetoacetate ester; (v) a beta-hydroxybutyrate free acid (i.e., beta-hydroxybutyric acid); and (vi) an acetoacetate free acid (i.e., acetoacetic acid). A stacked ketone body composition preferably includes a combination of ketone body compounds selected from (i) through (vi) such that there are at least two of: (A) one or more ketone body salts; (B) one or more ketone body esters; and (C) one or more ketone body free acids.

In addition, because beta-hydroxybutyrate has a chiral center, any of the salt, ester, and acid forms of beta-hydroxybutyrate can be R-beta-hydroxybutyrate, S-beta-hydroxybutyrate, a racemic mixture of R, S-beta-hydroxybutyrate, or a mixture enriched with R-beta-hydroxybutyrate or S-beta-hydroxybutyrate. R-beta-hydroxybutyrate is the endogenous form of beta-hydroxybutyrate produced by the body, while S-beta-hydroxybutyrate can be converted to R-beta-hydroxybutyrate, such as by enzymatic conversion to acetoacetate, which has no chiral center, and then to R-beta-hydroxybutyrate. Because R-beta-hydroxybutyrate is the endogenous form, it is more rapidly utilized by the body. Conversely, S-beta-hydroxybutyrate provides for slower, delayed available of available ketone bodies because it must first be converted to R-beta-hydroxybutyrate before it can be used as energy. Nevertheless, S-beta-hydroxybutyrate may have other benefits unrelated to energy, such as signaling. In view of the foregoing, stacked compositions can also include different amounts or rations of R-beta-hydroxybutyrate and S-beta-hydroxybutyrate.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

I. Definitions

Figure 1:
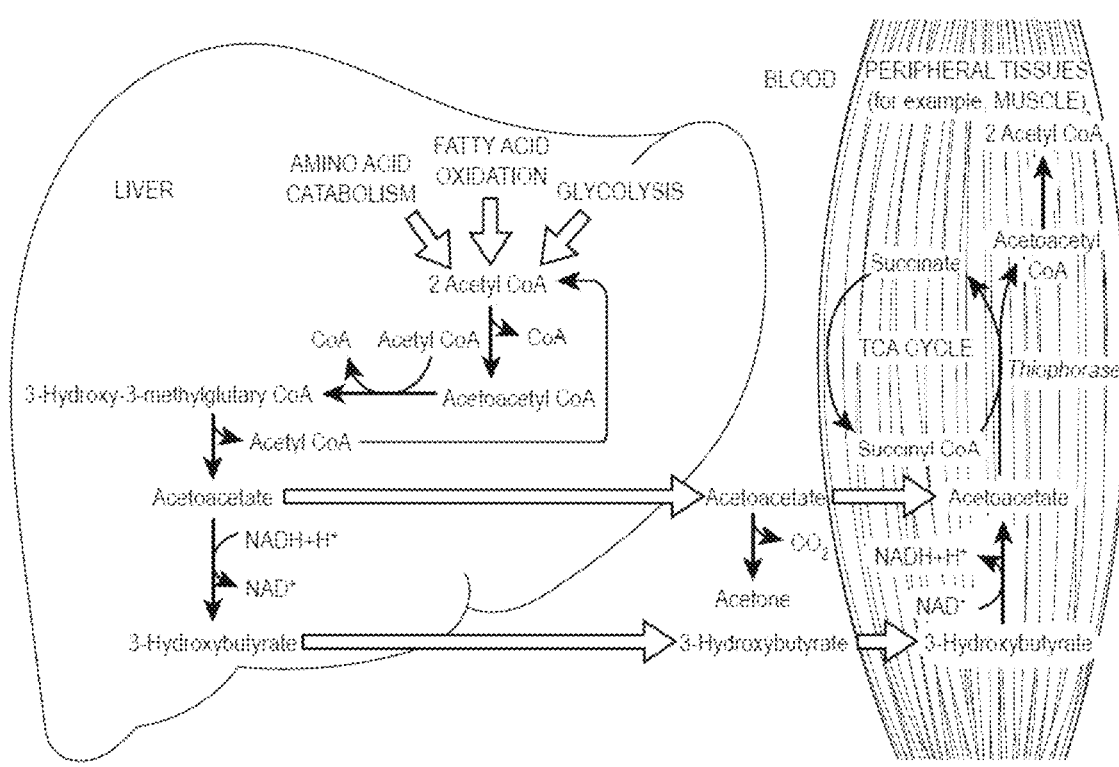
FIG. 1 schematically illustrates some of the metabolic pathways of ketosis, showing ketogenesis in the liver and ketolysis in peripheral tissues such as muscle.

The compound "beta-hydroxybutyrate," also known as β-hydroxybutyrate, 3-hydroxybutyrate, βHB, beta-hydroxybutyrate, or beta-hydroxybutyrate, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure shown below represents beta-hydroxybutyrate compounds that may be utilized in the disclosed compositions:

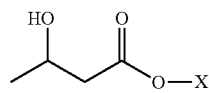

where,

X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

Beta-hydroxybutyrate may be utilized by a patient's body as an energy source during instances of low glucose levels in the subject or when a patient's body is supplemented with a usable form of beta-hydroxybutyrate. Although not technically a "ketone", one of skill in the art will recognize that beta-hydroxybutyrate, in the context of ketosis, is commonly referred to as a "ketone body".

The beta-hydroxybutyrate compound can be provided as a racemic mixture of enantiomers, or R,S-beta hydroxybutyrate (also known as DL-beta hydroxybutyrate), which can be made synthetically. In humans, the enantiomer R-beta-hydroxybutyrate ("D-3-hydroxybutyrate," "D-beta hydrobutyrate," or "D-beta-hydroxybutyrate") is synthesized in the liver from acetoacetate, the first ketone produced in the fasting. Therefore, it may be desirable to provide beta-hydroxybutyrate as the R-enantiomer to increase potency, either enriched relative to S-beta-hydroxybutyrate ("L-3-hydroxybutyrate," "L-beta hydrobutyrate," or "L-beta-hydroxybutyrate") or in purified form isolated from S-beta-hydroxybutyrate.

Alternatively, it may be desirable to provide beta-hydroxybutyrate as the S-enantiomer, either enriched relative to R-beta-hydroxybutyrate or in purified form isolated from R-beta-hydroxybutyrate. S-beta-hydroxybutyrate may be associated with one or more of: increased endogenous production of R-beta-hydroxybutyrate and acetoacetate; endogenous conversion of the S-beta-hydroxybutyrate into one or both of R-beta-hydroxybutyrate and acetoacetate; endogenous conversion of the S-beta-hydroxybutyrate into fatty acids and sterols; prolonged ketosis; metabolism of the S-beta-hydroxybutyrate independent of conversion to R-beta-hydroxybutyrate and/or acetoacetate; increased fetal development; increased growth years; reduced endogenous production of acetone during ketosis; signaling by the S-beta-hydroxybutyrate that modulates metabolism of R-beta-hydroxybutyrate and glucose; antioxidant activity; and production of acetyl-CoA.

Administering R-beta-hydroxybutyrate, the endogenous form, results in attaining relatively rapid elevated ketosis, while administering S-beta-hydroxybutyrate, which must first be converted to the R form, provides slower and more sustained ketosis. The different enantiomers may therefore be combined in different proportions to tailor a desired time release profile according to particular application needs or preferences.

The compound "acetoacetate" is the deprotonated form of acetoacetic acid, which is a carboxylic acid having the formula $CH_3COCH_2COOH$. The deprotonated form present at typical biological pH levels is therefore $CH_3COCH_2COO^-$. As with beta-hydroxybutyrate, acetoacetate may be utilized as an energy source during ketosis. The following general chemical structure represents acetoacetate compounds that may be utilized in the disclosed compositions (stereoisomers thereof may also be utilized):

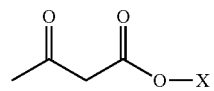

where,

X can be hydrogen, metal ion, amino cation, such as from an amino acid, alkyl, alkenyl, aryl, or acyl.

When X is a hydrogen, the compound is acetoacetic acid. When X is a metal ion or an amino cation, the compounds is an acetoacetate salt. When X is alkyl, alkenyl, aryl, or acyl, the compounds is an acetoacetate ester. The foregoing compounds can be in any desired physical form, such as crystalline, powder, solid, liquid, solution, suspension, or gel.

The beta-hydroxybutyrate and acetoacetate compounds described above may be collectively referred to herein as "ketone bodies," "exogenous ketone bodies," a "ketone body component," or "exogenous ketones."

The terms "stacked composition," "keto-stack," "stack," "ketone body stack," variations thereof, and the like are used herein to refer to a composition including at least two separate exogenous ketone bodies selected from the group consisting of: (i) a beta-hydroxybutyrate salt; (ii) an acetoacetate salt; (iii) a beta-hydroxybutyrate ester; (iv) an acetoacetate ester; (v) a beta-hydroxybutyrate free acid (i.e., beta-hydroxybutyric acid); and (vi) an acetoacetate free acid (i.e., acetoacetic acid).

Compounds (i) and (ii) represent different forms of "ketone body salts." Compounds (iii) and (iv) represent different forms of "ketone body esters." And compounds (v) and (vi) represent different forms of "ketone body free acids." A stacked ketone body composition preferably includes a combination of ketone body compounds selected from (i) through (vi) such that there are at least two of: (A) one or more ketone body salts; (B) one or more ketone body esters; and (C) one or more ketone body free acids.

In at least some instances, the particular exogenous ketone body (i.e., beta-hydroxybutyrate or acetoacetate) is referred to as the "ketone body component" while the particular salt, ester, or free acid portion is referred to as the "carrier component." For example, a sodium beta-hydroxybutyrate compound utilizes sodium as the carrier component and beta-hydroxybutyrate as the ketone body component, acetoacetic acid utilizes hydrogen as the carrier component and acetoacetate as the ketone body component, and a methyl beta-hydroxybutyrate utilizes a methyl group as the carrier component and beta-hydroxybutyrate as the ketone body component. The ester and/or salt forms of ketone bodies can be thought of as "carriers" for the acid form because they reduce acidity and harshness as compared to pure acid forms.

Some embodiments, in particular those that include a free acid form of an exogenous ketone body, may also include a "stabilizer" that functions to provide the exogenous ketone body in a more administrable form. For example, beta-hydroxybutyric acid and/or acetoacetic acid may be partially neutralized using a strong or weak base, such as an alkali or alkaline earth metal hydroxide, carbonate, or bicarbonate, basic amino acid, and the like. Following such a partial neutralization, the solution will also include a "salt" form as defined herein. But where the neutralization is only partial, and a certain molar excess of $H^+$ ions remains present, the solution will also include a proportion of the free acid form.

Some embodiments combine at least one beta-hydroxybutyrate compound with at least one acetoacetate compound.

Some embodiments optionally include a supplemental source of ketone body precursors in the form of fatty acids or esters thereof. A typical ester form of fatty acids is a mono-, di-, or triglyceride. Preferred forms of fatty acids and their esters are medium chain fatty acids, though short and/or long chain fatty acids and their esters may also be utilized. Providing a supplemental source of ketone body precursors can beneficially extend and/or elevate the effects of ketosis. That is, such supplemental sources can ensure that the body has sufficient "reserves" on hand for starting and maintaining ketosis in conjunction with the administered exogenous ketone bodies.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid and/or acetoacetic acid with a strong or weak base, such as an alkali or alkaline earth metal hydroxide, carbonate, or bicarbonate, basic amino acid, and the like.

Exemplary salt forms include sodium, potassium, calcium, and magnesium salts. Some embodiments include one or more transition metal salts. Transition metal cations suitable for use as part of a salt include lithium, chromium, manganese, cobalt, copper, zinc, iron, (e.g., as an iron II or iron III cation), molybdenum, and selenium. Other suitable salt forms include cations of amino acids or their derivatives, such as arginine, lysine, histidine, ornithine, creatine, agmatine, and citrulline. Suitable ester forms include mono-esters of ethanol, mono-esters of 1-propanol, mono-esters of 1,3-propanediol, di-esters of 1,3-propanediol, mono-esters of S-1,3-butanediol, di-esters of 1,3-butanediol, mono-esters of glycerin, di-esters of glycerin, and tri-esters of glycerin. 1,3-butanediol is a metabolic beta-hydroxybutyrate precursor that may be additionally or alternatively be utilized as a source of beta-hydroxybutyrate and/or acetoacetate compounds.

As used herein, "subject" or "patient" refers to mammals, including humans and other primates. The subject may be any mammal requiring metabolic therapy, treatment, or prophylaxis, or any mammal suspected of requiring metabolic therapy, treatment, or prophylaxis. Prophylaxis means that regiment is undertaken to prevent a possible occurrence, such as where a high risk of diabetes or other metabolic disorder is identified. "Patient" and "subject" are used interchangeably herein.

The term "unit dose" refers to a dosage form that is configured to deliver a specified quantity or dose of composition or component thereof. Example dosage forms include, but are not limited to, tablets, capsules, powders, food products, food additives, beverages, beverage additives, candies, suckers, pastilles, food supplements, sprays, injectables, and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, syringe, spoon, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

"Ketosis" as used herein refers to a subject having blood ketone levels within the range of about 0.5 mmol/L to about 16 mmol/L. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis," or it denotes an altered metabolism in which fat becomes the predominant energy source, consequently shifting the body from a state of fat storage to a state of fat oxidation.

The term "medium chain triglycerides" (MCT) refers to molecules having a glycerol backbone attached to three medium chain fatty acids. Medium chain fatty acids range from 6 to 12 carbon atoms in length. Exemplary fatty acids are caprylic acid, also known as octanoic acid, comprising 8 carbon molecules, and capric acid, also known as decanoic acid, comprising 10 carbon molecules. Because MCTs are ketone body precursors, including one or more MCTs may provide an additional source for the production of ketone bodies independent of the beta-hydroxybutyrate and acetoacetate compounds, thus helping to promote sustained elevation of ketone levels to a desired therapeutic level.

The term "short chain triglycerides" (SCT) refers to molecules similar to MCT molecules but with short chain fatty acids (6 carbon atoms or less in length, such as 5 carbon atoms or less) attached to the glycerol backbone. These can be provided in the form of mono-, di-, and triglycerides, other esters, salts, or free acids.

The term "long chain triglycerides" (LCT) refers to molecules similar to MCT molecules but with long chain fatty acids (12 carbon atoms or more in length, such as 13 carbon atoms or more) attached to the glycerol backbone.

Examples of short chain fatty acids include acetic acid, propionic acid, butyric acid, isobutyric acid, valeric acid, isovaleric acid, and caproic acid. Examples of medium chain fatty acids include caprylic acid, capric acid, and lauric acid. Examples of saturated long-chain fatty acids include myristic acid, palmitic acid, stearic acid, arachidic acid, behenic acid, lignoceric acid, and cerotic acid.

The term "administration" or "administering" is used herein to describe the process in which the ketogenic compositions are delivered to a subject. The composition may be administered in various ways including oral, intragastric, or parenteral (referring to intravenous and intra-arterial and other appropriate parenteral routes), among others.

II. Balancing Beta-Hydroxybutyrate and Acetoacetate

The administration of a combined beta-hydroxybutyrate/acetoacetate ketogenic composition results in elevated and sustained blood levels of ketone bodies, thereby exploiting the metabolic and physiological advantages of sustained ketosis. Raising the levels of ketone bodies in the blood to replicate the components of ketogenesis in a subject provides the subject with greater flexibility in diet options as compared to a method that aims to induce and sustain ketosis based on diet alone (e.g., based on fasting and/or limited carbohydrate intake). For example, a subject that has been administered appropriate amounts of beta-hydroxybutyrate and acetoacetate will be able to eat higher levels of carbohydrate or sugar-based food without jeopardizing their ketogenic state and shifting back into a glucose-based metabolic state, thus allowing them a much easier pathway to sustaining ketosis without the risk of metabolic confusion through toggling between glycolysis and ketosis.

Examples of beneficial effects of increased ketone body level in a subject include one or more of appetite suppression, weight loss, fat loss, reduced blood glucose level, improved mental alertness, increased physical energy, improved cognitive function, reduction in traumatic brain injury, reduction in effect of diabetes (e.g., type II diabetes), improvement of neurological disorder (e.g., ALS, Alzheimer's, Parkinson's), reduction of cancer, reduction of inflammation, anti-aging, anti-glycation, reduction in epileptic seizer, improved mood, increased strength, increased muscle mass, or improved body composition.

Further, such administration facilitates easier transitioning into a ketogenic state while reducing or eliminating the detrimental effects typically associated with entering ketosis, often referred to as the "keto flu," a very undesirable effect and often high-level deterrent from entering into a ketogenic advantaged state.

Embodiments disclosed herein provide a therapeutically effective amount of a combined beta-hydroxybutyrate/acetoacetate composition. Beneficially, the beta-hydroxybutyrate/acetoacetate composition is formulated to provide biologically balanced proportions of beta-hydroxybutyrate and acetoacetate in order to optimize the induction and/or sustainment of a ketogenic state in the user. For example, the combined beta-hydroxybutyrate/acetoacetate embodiments disclosed herein are capable of more effectively inducing and/or sustaining ketosis in a mammal as compared to an otherwise similar dosage regimen of beta-hydroxybutyrate alone or acetoacetate alone. Likewise, certain of the combined beta-hydroxybutyrate/acetoacetate embodiments disclosed herein are capable of more effectively inducing and/or sustaining ketosis in a mammal as compared to a composition that includes some unspecified amount of acetoacetate (likely some trivial amount).

FIG. 1 schematically illustrates the interplay between ketogenesis and ketolysis. Ketogenesis occurs in the liver, where a combination of catabolic processes breaks down amino acids, fatty acids, and/or glycogen to generate the ketone bodies acetoacetate and beta-hydroxybutyrate. The majority of these ketone bodies will typically be produced through fatty acid oxidation.

Although beta-hydroxybutyrate is the more reduced compound, both beta-hydroxybutyrate and acetoacetate are passed into the bloodstream and delivered to peripheral tissues to be used as an energy source. As shown, acetoacetate may be directly utilized in the TCA cycle (i.e., citric acid cycle), whereas beta-hydroxybutyrate is first oxidized by $NAD^+$ into acetoacetate before the resulting acetoacetate is incorporated into the TCA cycle.

With reference again to FIG. 1, the benefits of the combined beta-hydroxybutyrate/acetoacetate compositions described herein will be explained, in particular with regards to the benefits of $NAD^+$ sparing. When a subject is in ketosis, the energy profile is already favorable for $NAD^+$ sparing as compared to when glucose is primarily used for energy. Stacking the separate ketone body components beta-hydroxybutyrate and acetoacetate can beneficially further spare $NAD^+$, as explained below.

As shown, during ketolysis, the available acetoacetate is directly incorporated into the TCA cycle and does not need to be initially oxidized by an $NAD^+$ molecule. During endogenous ketosis (e.g., as a result of fasting), the use of these $NAD^+$ molecules to convert beta-hydroxybutyrate to acetoacetate in peripheral tissues (ketolysis) is essentially balanced by the countervailing generation of $NAD^+$ molecules to convert acetoacetate to beta-hydroxybutyrate in the liver (ketogenesis).

However, when a user is supplementing with exogenous beta-hydroxybutyrate, the use of $NAD^+$ in the peripheral tissues is not balanced in the same way by the generation of $NAD^+$ in the liver. Supplementation of exogenous beta-hydroxybutyrate therefore creates an increase in $NAD^+$ demand on the user. Low levels of $NAD^+$ are associated with aging and declining mitochondrial function. See, for example, Shin-ichiro Imai and Leonard Guarente, "$NAD^+$ and Sirtuins in Aging and Disease," Trends Cell Biol. 2014 Aug. 24(8), 464-471; Massudi H et al., "Age-associated changes in oxidative stress and $NAD^+$ metabolism in human tissue," PLoS One, 2012, 7(7):e42357; Carlos Canto and Johan Auwerx, "Targeting Sirtuin 1 to Improve Metabolism:

All you Need is NAD+?" Pharm. Rev. January 2012, 64(1) 166-187. In addition, low NAD+ relative to NADH can set in motion some of the same physiological responses to low NAD+ associated with low oxygen levels, even if actual oxygen levels are accurate. See Gomes A P et al. "Declining NAD(+) induces a pseudohypoxic state disrupting nuclear-mitochondrial communication during aging" Cell, 2013 Dec. 19, 155(7).

An exogenous ketogenic composition with an increased proportion of acetoacetate relative to beta-hydroxybutyrate can therefore reduce the depletion of NAD+ as compared to a composition having higher levels of beta-hydroxybutyrate. Compositions described herein include effective levels of acetoacetate in combination with beta-hydroxybutyrate in order to achieve these benefits.

In general, beta-hydroxybutyrate is the primary "energy" ketone body, and having too high of a ratio of acetoacetate to beta-hydroxybutyrate may restrict the ability to obtain a desired energy boost. In some cases, excessive acetoacetate can also introduce undesirable effects. Referring again to FIG. 1, an amount of acetoacetate circulating in the blood will spontaneously convert to $CO_2$ and acetone. High levels of acetone can be undesirable. Elevated acetone levels can, for example, represent inefficient use of energy by indicating that acetoacetate is not being converted to beta-hydroxybutyrate or being appropriately used in the TCA cycle. Further, although the human body is typically able to manage normal ketosis-related acetone levels, physiologically clearing excess acetone can be taxing on the liver. In addition to these primary physiological impacts, excess acetone an also cause unpleasant "keto breath." Exogenous beta-hydroxybutyrate supplementation minimizes acetone generation because beta-hydroxybutyrate is typically not converted into acetoacetate until reaching the peripheral tissues where it is used.

For these reasons, the benefits of increasing the levels of acetoacetate relative to beta-hydroxybutyrate must be balanced against the detrimental effects of excessive acetoacetate. In one embodiment, a ketogenic composition includes a combination of beta-hydroxybutyrate and acetoacetate, with the acetoacetate being included in an amount that is at least about 10%, at least about 20%, at least about 30%, or at least about 40% w/w of the beta-hydroxybutyrate and acetoacetate mixture.

At the same time, an optimized balance of beta-hydroxybutyrate and acetoacetate is typically where acetoacetate component is limited to no more than about 45% of the beta-hydroxybutyrate and acetoacetate mixture. In other words, an optimized weight ratio of beta-hydroxybutyrate to acetoacetate may be about 19:1, about 16:1, about 14:1, about 12:1, about 9:1, about 6:1, about 4:1, about 3:1, about 7:3, about 1.5:1, about 1.22:1, and ranges defined by these ratios. Formulations having these ratios beneficially ensure that there is sufficient acetoacetate in proportion to the beta-hydroxybutyrate to provide the effective ketogenic properties described herein without causing the detrimental effects associated with excess acetoacetate. Regulating the amount of each separate ketone body component beneficially allows for tailored compositions that are optimized for particular needs or preferences. As described in more detail below, the relative amounts of beta-hydroxybutyrate and acetoacetate may be adjusted and optimized based on a subject's age, health, activity level, desired dosage regimen, and/or liver sensitivity, for example.

In general, subjects that may be deficient in NAD+, such as more elderly (e.g., those over 55, those over 60, those over 65, or those over 70) or infirm people, may benefit from higher relative amounts of acetoacetate, such as between about 25% to about 45% acetoacetate, or about 30% to about 45% acetoacetate, or about 35% to about 45% acetoacetate of the beta-hydroxybutyrate and acetoacetate mixture. In addition, the compositions disclosed herein may contain supplemental NAD+.

Similarly, subjects that are not deficient in NAD+, such as healthier, younger people, may benefit from lower relative amounts of acetoacetate, such as between about 5% to about 25% acetoacetate, or about 8% to about 22% acetoacetate, or about 10% to about 20% acetoacetate of the beta-hydroxybutyrate and acetoacetate mixture.

The ketogenic compositions described herein may be provided within a dosage regimen effective for inducing and sustaining ketosis. For example, the combined beta-hydroxybutyrate and acetoacetate mass in a daily dose may range from about 0.5 gram to about 50 grams, or about 0.75 gram to about 25 grams, or about 1 gram to about 15 grams, or about 1.5 grams to about 12 grams. The daily dose may be provided as a single daily dose or as a multiple dose (e.g., 2, 3, or 4 times daily).

The beta-hydroxybutyrate may be provided as the free acid, as a salt, as a mixed salt, as an ester, or as explained in greater detail below, as a "stacked" combination thereof. When provided in salt form, beta-hydroxybutyrate salts may include sodium, potassium, calcium, magnesium, or suitable transition metal (e.g., zinc, iron, molybdenum, or selenium) as cations, for example. Some embodiments may additionally or alternatively include cations as one or more amino acids or other organic compounds that have a net positive charge at the pH at which the beta-hydroxybutyrate salts are produced. Suitable amino acids for this purpose can include amino acids that contain more than one amine group capable of being protonated to form a compound having a net positive charge, which can provide the counter cation for beta-hydroxybutyrate anion. Examples include arginine, lysine, leucine, iso-leucine, histidine, ornithine, citrulline, L-glutamine, or other suitable amino acids or metabolites of amino acids (e.g., creatine).

In some embodiments, a ketogenic composition may also include other ketone body precursors, such as one or more medium chain fatty acids or one or more mono-, di-, or triglycerides of one or more medium chain fatty acids. Including one or more medium chain fatty acids, or a mono-, di-, or triglyceride of one or more medium chain fatty acids can provide an additional source for the production of ketone bodies independent of the beta-hydroxybutyrate or acetoacetate. In order words, the beta-hydroxybutyrate and acetoacetate compounds promote more rapid achievement of ketosis in the body while the medium chain fatty acid or a mono-, di-, or triglyceride of a medium chain fatty acid helps sustain the body in a state of ketosis once the exogenous beta-hydroxybutyrate and acetoacetate molecules have already been consumed by the body. Including at least one of MCT, medium chain fatty acid, or mono-, di-, or triglyceride of a medium chain fatty acid can help sustain ketosis over a longer period of time without having to provide more exogenous beta-hydroxybutyrate and acetoacetate.

The at least one medium chain fatty acid has from 6 to 12 carbons, preferably from 8 to 10 carbons. Compositions and methods related to the combination of beta-hydroxybutyrate with a medium chain fatty acid, or ester thereof, are disclosed in U.S. Pat. No. 9,138,420, which patent is incorporated herein by this reference in its entirety.

In addition to or instead of the one or more medium chain fatty acids or one or more mono-, di-, or triglycerides of one or more medium chain fatty acids, ketogenic compositions may include one or more short and/or long chain fatty acids or one or more mono-, di-, or triglycerides of one or more short and/or long chain fatty acids. Short chain fatty acids typically have fewer than 6 carbons, and long chain fatty acids typically have more than 12 carbons.

Examples and sources of the medium chain fatty acid, or an ester thereof such as a medium chain triglyceride, include coconut oil, coconut milk powder, fractionated coconut oil, palm oil, palm kernel oil, caprilic acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

Notwithstanding the foregoing, there is a practical limit to how much MCT or other medium chain fatty acid source an individual can take, with some individuals having lower tolerance for MCT or other medium chain fatty acid sources (e.g., they may cause gastrointestinal issues).

In some embodiments, the ketogenic composition may be provided as a solid or powder form. Solid or powder ketogenic compositions may include one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), phosphate salt (e.g., tricalcium phosphate), talcum, powdered cellulose, and the like.

In alternative embodiments, the ketogenic composition may be provided as a liquid, such as in the form of a shot or mouth spray for fast delivery and absorption, or as a gel. Liquid or gel forms may include one or more carriers, such as water, ethanol, glycerin, propylene glycol, 1,3-propandiol, and the like, into which the beta-hydroxybutyrate/acetoacetate compounds are dissolved or dispersed. The composition may include flavoring agents that help mask the somewhat poor taste of beta-hydroxybutyrate compounds. These flavoring agents may include essential oils, such as peppermint, natural and artificial sweeteners, and other flavorants known in the art.

The ketogenic composition may include one or more supplements known in the art, such as vitamins, minerals, and caffeine or other stimulants. For example, the ketogenic composition may further comprise vitamin $D_3$, such as in an amount of about 5 µg to about 200 µg, or about 10 µg to about 100 µg, or about 15 µg to about 75 µg, or in an amount of about 200 IU to about 8000 IU, or about 400 IU to about 4000 IU, or about 600 IU to about 3000 IU. Caffeine may be included in an amount of about 10 mg to about 250 mg, or about 25 mg to about 170 mg, or about 40 mg to about 120 mg.

III. Stacking Different Forms of Ketone Bodies

As described above, the exogenous ketone bodies described herein may be provided in three general forms: 1) salt form, 2) ester form, and 3) free acid form (i.e., beta-hydroxybutyric acid or acetoacetic acid). Beta-hydroxybutyric acid can be provided as the R-enantiomer, S-enantiomer, racemic mixture, or enriched with the R- or S-enantiomer. The compositions described herein may be provided in any one of these forms or as a "stacked" mixture combining at least two of these forms.

Each of the different forms has its own properties and its own potential benefits and limitations. For example, ester forms of beta-hydroxybutyrate or acetoacetate typically have poor organoleptic properties relative to the other forms. In addition, ester forms of beta-hydroxybutyrate or acetoacetate are often described as having a pungent taste and/or smell.

Salt forms of beta-hydroxybutyrate or acetoacetate are generally considered to taste better than ester forms. However, administration of clinically or dietetically effective doses of exogenous ketone bodies in salt form inherently requires administration of relatively high levels of the corresponding cations. Sodium, for example, is often used as the cation in ketone body salts, and high levels of sodium have well-known negative health effects. Excessive amounts of potassium and calcium should also be avoided. Although different salts having different cations may be mixed to dilute the impact of a single cation, it can still be difficult to provide effective amounts of beta-hydroxybutyrate and/or acetoacetate without upsetting the electrolyte balance in the subject/patient.

The free acid forms may also be utilized. However, because beta-hydroxybutyric acid has a pKa of 4.70, it deprotonates and produces $H^+$ at physiological pH. Similarly, acetoacetic acid has a pKa of 3.59 and likewise deprotonated and produces $H^+$ at physiological pH. The resulting excess acidity can cause undesirable side effects including causing or aggravating gastrointestinal issues such as ulcers or reflux.

The free acid form of acetoacetate is the least stable form (meaning that it can decompose to acetone and carbon dioxide), with the salt form being somewhat more stable and the ester form being significantly more stable. The acid form has a half-life of 140 minutes at 37° C. in water, whereas the basic form (the anion in a salt form) has a half-life of 130 hours. That is, it decomposes about 55 times more slowly. Esters are far more stable and can persist for weeks, months, or years depending on storage conditions.

Combining different forms of exogenous ketone bodies can beneficially limit the occurrence and/or severity of these undesirable side-effects and/or can permit administration of higher doses of exogenous ketone bodies. For example, a ketone body stack can deliver the same amount of exogenous ketones as a single form without causing the same occurrence and/or severity of side-effects. Likewise, a combined form can deliver a greater amount of exogenous ketones than a single form before reaching similar occurrence and/or severity of side-effects.

Figure 2A:
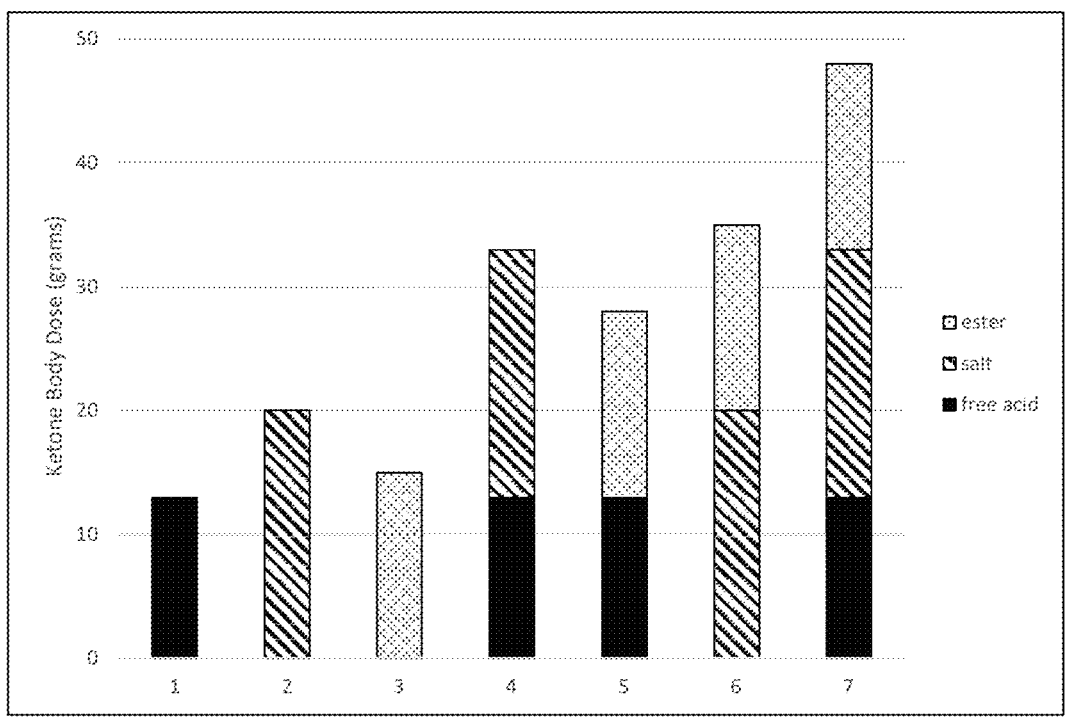
FIG. 2A illustrates higher levels of exogenous ketone bodies that may be administered when using a "stacked" dose of at least two different forms of exogenous ketone bodies as compared to single forms of the exogenous ketone body.
Figure 2B:
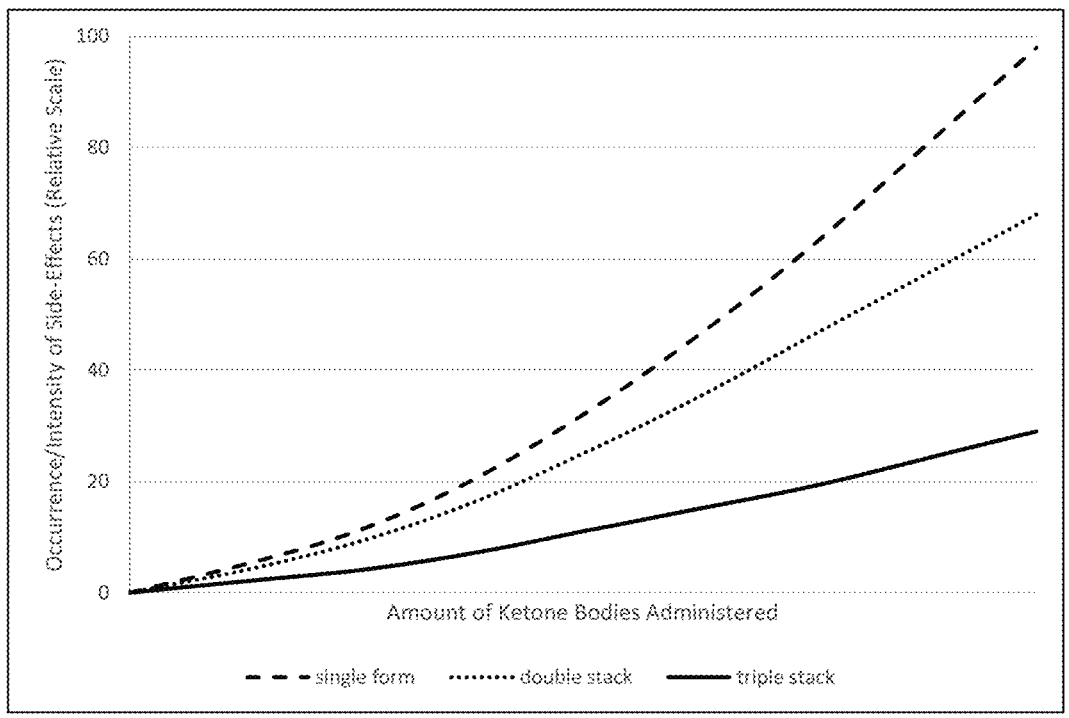
FIG. 2B illustrates expected relative rates of undesirable side-effects resulting from treatment with various formulations of exogenous ketone bodies, where a "triple stack" formulation comprising each of 1) a salt form of an exogenous ketone body, 2) an ester form of an exogenous ketone body, and 3) a free acid form of an exogenous ketone body (i.e., beta-hydroxybutyric acid and/or acetoacetic acid) is expected to allow for administration of a greater amount of exogenous ketone bodies and/or less occurrence or intensity of side-effects as compared to a "double stack" comprising only two such forms of exogenous ketone bodies, and where both the triple stack and double stack formulations are expected to allow for administration of a greater amount of exogenous ketone bodies and/or less occurrence or intensity of side-effects as compared to administration of a "single form" comprising only a single such form of an exogenous ketone body.

This is schematically illustrated in FIGS. 2A and 2B. FIG. 2A shows different exogenous ketone doses when using a single form (formulations 1-3), a double stack (formulations 4-6), and a triple stack (formulation 7). Although individual tolerances may vary and the illustrated doses are therefore exemplary only, a typical subject will want to avoid excessive amounts of any single form of exogenous ketones in order to avoid the corresponding side effects.

Accordingly, stacking different forms of exogenous ketones allows for greater delivery of exogenous ketones in a dose and/or allows for a higher dosing frequency as compared to use of the single form. For example, different forms of exogenous ketones may be stacked in a single dose to allow for greater amounts of exogenous ketones in the dose, and/or different forms of exogenous ketones may be taken in different doses throughout the day to allow for greater dosing frequency and thus higher overall daily delivery of exogenous ketones.

A single dose of stacked ketones can also provide more sustained levels of ketone bodies in the blood as compared to an otherwise similar amount provided in a single form. For example, a stacked formulation can be tailored to provide a more preferable release profile, such as one that combines the benefits of more rapid onset with the benefits of a more extended release, and/or one that provides an overall greater pharmacokinetic area under the curve (AUC).

FIG. 2B shows expected relative severity of undesirable side-effects resulting from treatment with various formulations of exogenous ketones, including stacked formulations. The triple stack formulation comprising each of 1) a salt form of an exogenous ketone, 2) an ester form of an exogenous ketone, and 3) a free acid form of an exogenous ketone is expected to allow for administration of a greater amount of exogenous ketones and/or to have reduced side-effects as compared to a double stack comprising only two such forms of exogenous ketones. Both the triple stack and the double stack are likewise expected to allow for administration of a greater amount of exogenous ketones and/or to have reduced side-effects as compared to a single form comprising only one form of exogenous ketone.

In other words, for a given dose of exogenous ketones, the triple stack can be formulated to cause less 1) organoleptic side-effects, 2) electrolyte imbalance side-effects, and/or 3) acidity side-effects as compared to the double stack or single form. For example, a single form ketones body ester may have a threshold dosage that the typical user will not exceed because of the negative organoleptic side-effects, a single form ketone body salt may have a threshold dosage limited by the recommended dietary limits of the electrolytes administered with the salt, and a single form ketone body free acid may have a threshold dosage that the typical user will not exceed because of the negative effects of acidity. The stacked forms of exogenous ketones, and in particular the exogenous ketone triple stack, allows for supplementation of greater amounts of exogenous ketones without passing any of the separate thresholds related to organoleptic, electrolyte, or acidity side-effects.

In some embodiments, a beta-hydroxybutyrate stack includes at least two of: (i) one or more exogenous ketone salts; (ii) one or more exogenous ketone esters; and (iii) an exogenous ketone body acid (beta-hydroxybutyric acid and/or acetoacetic acid). For example, an exogenous ketone double stack may include at least two of components (i), (ii), and (iii) each provided at about 2% to about 98%, or about 5% to about 95%, or about, 10% to about 90%, or about 20% to about 80%, or about 30% to about 70%, or about 40% to about 60% on a molar basis of the ketone body component.

In some embodiments, a ketone body triple stack includes a ketone body ester at about 2% to about 96%, or about 5% to about 90%, or about 10% to about 80%, or about 20% to about 60% on a molar basis of the ketone body component, includes a ketone body salt at about 2% to about 96%, or about 5% to about 90%, or about 10% to about 80%, or about 20% to about 60% on a molar basis of the ketone body component, and includes a free acid form at about 2% to about 96%, or about 5% to about 90%, or about 10% to about 80%, or about 20% to about 60% on a molar basis of the ketone body component. In some embodiments, a triple stack includes each of the three carrier component forms in substantially equal amounts on a molar basis of the ketone body component.

A ketone body stack may also provide a more beneficial digestive release profile. Each of the different carrier component forms may interact somewhat differently upon ingestion. For example, the free acid form may be readily delivered to the bloodstream as a usable ketone body, whereas ketone bodies from salt forms may in general take slightly longer to reach the bloodstream depending on the solubility characteristics of the particular salt or salt mixture utilized, and ester forms may in general take the longest to reach the bloodstream depending on how rapidly the ester bond undergoes hydrolysis. Thus, a stacked formulation can be tailored to provide a more preferable release profile, such as one that combines the benefits of more rapid onset with the benefits of a more extended release, and/or one that provides an overall greater pharmacokinetic area under the curve (AUC).

Figure 3:
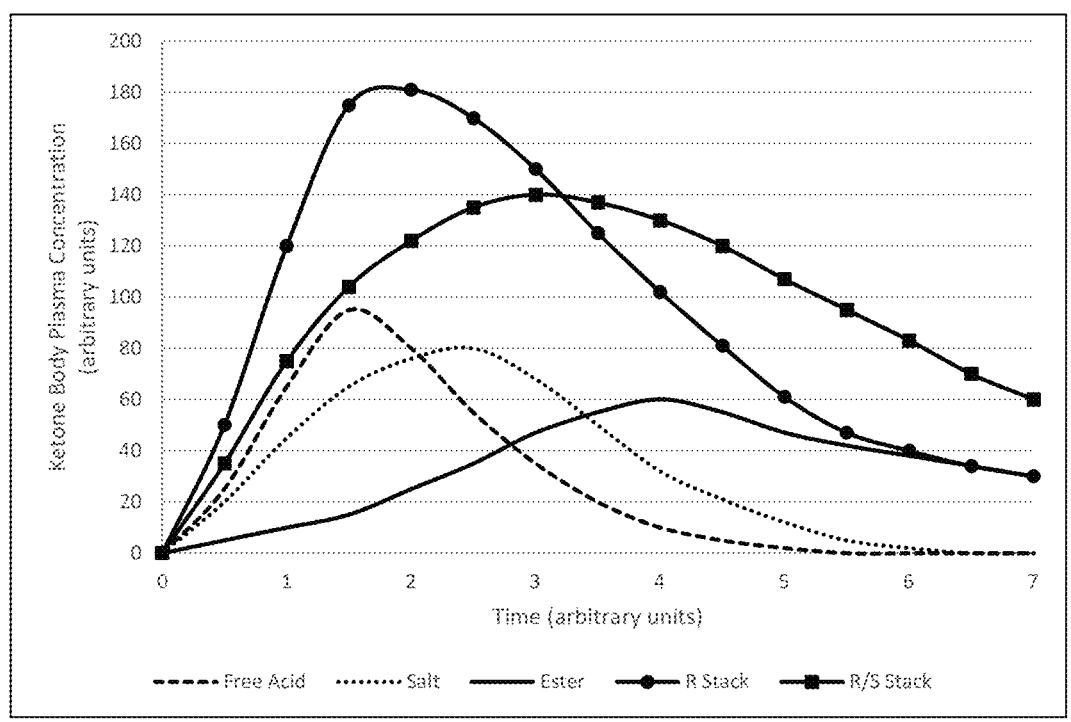
FIG. 3 compares expected release profiles of stacked compositions (e.g., R-beta-hydroxybutyrate comprising each of the free acid, salt, and ester forms and R,S-beta-hydroxybutyrate) to each of the free acid, salt, and ester single forms, illustrating that stacked compositions may provide an overall release profile that is extended and has a larger area under the curve (AUC).

This is illustrated in FIG. 3, which compares expected release profiles of keto stack compositions (e.g., comprising each of the free acid, salt, and ester forms) to each of the free acid, salt, and ester single forms. Because the keto stack compositions are able to provide more overall exogenous ketone bodies, and because they are provided in a plurality of different forms with different release characteristics, the overall release profile is extended and provides a larger AUC.

FIG. 3 also illustrates how a release profile may be adjusted by utilizing different relative amounts of S-beta-hydroxybutyrate and R-beta-hydroxybutyrate. As illustrated, the beta-hydroxybutyrate in the "R Stack" is substantially comprised of R-beta-hydroxybutyrate, while the "R/S Stack" replaces some of the R-beta-hydroxybutyrate with S-beta-hydroxybutyrate to flatten and extend the release profile.

Given that there are three separate "carrier component" forms and two different "ketone body component" types, there are multiple keto stack combinations that may be formulated. As reproduced below, Table 1 illustrates several exemplary stacked combinations having 2, 3, 4, 5, or 6 different compound types making up the stack.

TABLE 1

| Combo No. | BHB Salts | BHB Ester | BHB Acid | ACAC Salt | ACAC Ester | ACAC Acid |
|---|---|---|---|---|---|---|
| 2-part stacks ||||||| 
| 1 | x | x | | | | |
| 2 | x | | x | | | |
| 3 | x | | | x | | |
| 4 | x | | | | x | |
| 5 | x | | | | | x |
| 6 | | x | x | | | |
| 7 | | x | | x | | |
| 8 | | x | | | x | |
| 9 | | x | | | | x |
| 10 | | | x | x | | |
| 11 | | | x | | x | |
| 12 | | | x | | | x |
| 13 | | | | x | x | |
| 14 | | | | x | | x |
| 15 | | | | | x | x |
| 3-part stacks ||||||| 
| 16 | x | x | x | | | |
| 17 | x | x | | x | | |
| 18 | x | x | | | x | |
| 19 | x | x | | | | x |
| 20 | | x | x | x | | |
| 21 | | x | x | | x | |
| 22 | | x | x | | | x |
| 23 | | | x | x | x | |

TABLE 1-continued

| Combo No. | BHB Salts | BHB Ester | BHB Acid | ACAC Salt | ACAC Ester | ACAC Acid |
|---|---|---|---|---|---|---|
| 24 |   |   | x | x |   | x |
| 25 | x |   | x | x |   |   |
| 26 |   |   |   | x | x | x |
| 4-part stacks |
| 27 | x | x | x | x |   |   |
| 28 | x | x | x |   | x |   |
| 29 | x | x | x |   |   | x |
| 30 |   | x | x | x | x |   |
| 31 |   | x | x | x |   | x |
| 32 |   | x | x | x | x | x |
| 33 |   | x | x |   | x | x |
| 34 | x | x |   |   | x | x |
| 35 | x | x |   | x | x |   |
| 5-part stacks |
| 36 | x | x | x | x | x |   |
| 37 | x | x | x | x |   | x |
| 38 |   | x | x | x | x | x |
| 39 | x |   | x | x | x | x |
| 40 | x | x |   | x | x | x |
| 6-part stack |
| 41 | x | x | x | x | x | x |

IV. Administration

Ketogenic compositions described herein may be administered to a subject in therapeutically effective dosages and/or in frequencies to induce or sustain ketosis. The combined beta-hydroxybutyrate and acetoacetate mass in a daily dose may range from about 0.5 gram to about 50 grams, or about 0.75 gram to about 25 grams, or about 1 gram to about 15 grams, or about 1.5 grams to about 12 grams.

In some embodiments, the compositions may further include one or more medium chain fatty acids, fatty acid esters, or mono-, di- or triglycerides of medium chain fatty acids in order to provide an additional source of ketone bodies for sustaining ketosis for a longer period of time compared to if just the beta-hydroxybutyrate/acetoacetate combination were used by itself. In some embodiments, the composition is preferably administered such that the ratio of beta-hydroxybutyrate/acetoacetate to medium chain fatty acid (or ester thereof) ranges from about 4:1 to about 1:4, or from about 2:1 to about 1:2, or from about 1.5:1 to about 1:1.5.

In alternative embodiments, the compositions may further include one or more short and/or long chain fatty acids, fatty acid esters, or mono-, di- or triglycerides of short and/or long chain fatty acids in order to provide an additional source of ketone bodies for sustaining ketosis. In some embodiments, the composition is preferably administered such that the ratio of beta-hydroxybutyrate/acetoacetate to medium, short and/or long chain fatty acid (or ester thereof) ranges from about 4:1 to about 1:4, or from about 2:1 to about 1:2, or from about 1.5:1 to about 1:1.5.

In some embodiments, the subject preferably follows a ketogenic diet that restricts intake of carbohydrates and protein during the period of administration of the composition. In one example embodiment, the subject may restrict the dietary intake to a ratio of about 65% fat, about 25% protein, and about 10% carbohydrates. The resulting therapeutic ketosis provides a rapid and sustained keto-adaptation as a metabolic therapy for a wide range of metabolic disorders, and provides nutritional support for therapeutic fasting, weight loss, and performance enhancement. As such, the composition is typically administered once per day, twice per day, or three times per day to a subject desiring to promote and/or sustain a state of ketosis.

In a preferred embodiment, a ketogenic composition is administered via oral administration of the composition in a solid, powdered form or liquid, such as in a powdered mixture (e.g., powder filled gelatin capsules), hard-pressed tablets, or other oral administration route known to those skilled in the art.

In some embodiments, multiple doses of the composition are administered. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etcetera.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo (i.e., therapeutic ketosis). In accordance with the present disclosure, a suitable single dose size is a dose that is capable of preventing or alleviating (reducing or eliminating) a symptom in a patient when administered one or more times over a suitable time period.

The amount of composition administered will depend on potency, absorption, distribution, metabolism, and excretion rates of the composition components, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once over a given time period (e.g., once per day), or may be divided and administered over intervals of time. It is to be understood that administration may be adjusted according to individual need and professional judgment of a person administrating or supervising the administration of the compositions.

V. Examples

The following is a description of exemplary combined beta-hydroxybutyrate/acetoacetate compositions useful for inducing and/or sustaining a ketogenic state in a subject to which they are administered. It should be appreciated that the beta-hydroxybutyrate and acetoacetate compounds described in the examples can be in the form of salts, esters, dimers, trimers, oligomers, and polymers, as discussed herein. The compositions can also be combined with medium chain fatty acids, esters, glycerides, and other supplements as disclosed herein to provide a desired level of elevated ketone bodies and other effects.

Example 1

A combined beta-hydroxybutyrate/acetoacetate composition is prepared by mixing beta-hydroxybutyrate with acetoacetate. The acetoacetate is added at 10% the weight of the beta-hydroxybutyrate/acetoacetate mixture. Compared to a similar dosage of beta-hydroxybutyrate without acetoacetate, the combined beta-hydroxybutyrate/acetoacetate composition limits the reduction of available NAD$^+$ in the subject. At the same time, the amount of acetoacetate is not so high as to cause unwanted effects associated with high levels of acetone in the blood.

The beta-hydroxybutyrate/acetoacetate composition is readily administered as a ketogenic composition, such as in powder, liquid or gel form as a dietary supplement mixed with food or drink, in the form of one or more capsules or tablets, or in liquid form such as a mouth spray or energy shot.

Example 2

A combined beta-hydroxybutyrate/acetoacetate composition is prepared by mixing beta-hydroxybutyrate with acetoacetate. The acetoacetate is added at 15% the weight of the beta-hydroxybutyrate/acetoacetate mixture. Compared to a similar dosage of beta-hydroxybutyrate without acetoacetate, the combined beta-hydroxybutyrate/acetoacetate composition limits the reduction of available NAD$^+$ in the subject. At the same time, the amount of acetoacetate is not so high as to cause unwanted effects associated with high levels of acetone in the blood.

The beta-hydroxybutyrate/acetoacetate composition is readily administered as a ketogenic composition, such as in powder, liquid or gel form as a dietary supplement mixed with food or drink, in the form of one or more capsules or tablets, or in liquid form such as a mouth spray or energy shot.

Example 3

A combined beta-hydroxybutyrate/acetoacetate composition is prepared by mixing beta-hydroxybutyrate with acetoacetate. The acetoacetate is added at 20% the weight of the beta-hydroxybutyrate/acetoacetate mixture. Compared to a similar dosage of beta-hydroxybutyrate without acetoacetate, the combined beta-hydroxybutyrate/acetoacetate composition limits the reduction of available NAD$^+$ in the subject. At the same time, the amount of acetoacetate is not so high as to cause unwanted effects associated with high levels of acetone in the blood.

The beta-hydroxybutyrate/acetoacetate composition is readily administered as a ketogenic composition, such as in powder, liquid or gel form as a dietary supplement mixed with food or drink, in the form of one or more capsules or tablets, or in liquid form such as a mouth spray or energy shot.

Example 4

A combined beta-hydroxybutyrate/acetoacetate composition is prepared by mixing beta-hydroxybutyrate with acetoacetate. The acetoacetate is added at 25% the weight of the beta-hydroxybutyrate/acetoacetate mixture. Compared to a similar dosage of beta-hydroxybutyrate without acetoacetate, the combined beta-hydroxybutyrate/acetoacetate composition limits the reduction of available NAD$^+$ in the subject. At the same time, the amount of acetoacetate is not so high as to cause unwanted effects associated with high levels of acetone in the blood.

The beta-hydroxybutyrate/acetoacetate composition is readily administered as a ketogenic composition, such as in powder, liquid or gel form as a dietary supplement mixed with food or drink, in the form of one or more capsules or tablets, or in liquid form such as a mouth spray or energy shot.

Example 5

A combined beta-hydroxybutyrate/acetoacetate composition is prepared by mixing beta-hydroxybutyrate with acetoacetate. The acetoacetate is added at 30% the weight of the beta-hydroxybutyrate/acetoacetate mixture. Compared to a similar dosage of beta-hydroxybutyrate without acetoacetate, the combined beta-hydroxybutyrate/acetoacetate composition limits the reduction of available NAD$^+$ in the subject. At the same time, the amount of acetoacetate is not so high as to cause unwanted effects associated with high levels of acetone in the blood.

The beta-hydroxybutyrate/acetoacetate composition is readily administered as a ketogenic composition, such as in powder, liquid or gel form as a dietary supplement mixed with food or drink, in the form of one or more capsules or tablets, or in liquid form such as a mouth spray or energy shot.

Example 6

A combined beta-hydroxybutyrate/acetoacetate composition is prepared by mixing beta-hydroxybutyrate with acetoacetate. The acetoacetate is added at 35% the weight of the beta-hydroxybutyrate/acetoacetate mixture. Compared to a similar dosage of beta-hydroxybutyrate without acetoacetate, the combined beta-hydroxybutyrate/acetoacetate composition limits the reduction of available NAD$^+$ in the subject. At the same time, the amount of acetoacetate is not so high as to cause unwanted effects associated with high levels of acetone in the blood.

The beta-hydroxybutyrate/acetoacetate composition is readily administered as a ketogenic composition, such as in powder, liquid or gel form as a dietary supplement mixed with food or drink, in the form of one or more capsules or tablets, or in liquid form such as a mouth spray or energy shot.

Example 7

A combined beta-hydroxybutyrate/acetoacetate composition is prepared by mixing beta-hydroxybutyrate with acetoacetate. The acetoacetate is added at 40% the weight of the beta-hydroxybutyrate/acetoacetate mixture. Compared to a similar dosage of beta-hydroxybutyrate without acetoacetate, the combined beta-hydroxybutyrate/acetoacetate composition limits the reduction of available NAD$^+$ in the subject. At the same time, the amount of acetoacetate is not so high as to cause unwanted effects associated with high levels of acetone in the blood.

The beta-hydroxybutyrate/acetoacetate composition is readily administered as a ketogenic composition, such as in powder, liquid or gel form as a dietary supplement mixed with food or drink, in the form of one or more capsules or tablets, or in liquid form such as a mouth spray or energy shot.

Example 8

A combined beta-hydroxybutyrate/acetoacetate composition is prepared by mixing beta-hydroxybutyrate with acetoacetate. The acetoacetate is added at 45% the weight of the beta-hydroxybutyrate/acetoacetate mixture. Compared to a similar dosage of beta-hydroxybutyrate without acetoacetate, the combined beta-hydroxybutyrate/acetoacetate composition limits the reduction of available NAD$^+$ in the subject. At the same time, the amount of acetoacetate is not so high as to cause unwanted effects associated with high levels of acetone in the blood.

The beta-hydroxybutyrate/acetoacetate composition is readily administered as a ketogenic composition, such as in powder, liquid or gel form as a dietary supplement mixed with food or drink, in the form of one or more capsules or tablets, or in liquid form such as a mouth spray or energy shot.

Example 9

A combined beta-hydroxybutyrate/acetoacetate composition is prepared by mixing beta-hydroxybutyrate with acetoacetate. The acetoacetate is added at 5% the weight of the beta-hydroxybutyrate/acetoacetate mixture. Compared to a similar dosage of beta-hydroxybutyrate without acetoacetate, the combined beta-hydroxybutyrate/acetoacetate composition reduces depletion of available NAD$^+$ in the subject. At the same time, the amount of acetoacetate low and limits unwanted effects associated with high levels of acetone in the blood.

The beta-hydroxybutyrate/acetoacetate composition is readily administered as a ketogenic composition, such as in powder, liquid or gel form as a dietary supplement mixed with food or drink, in the form of one or more capsules or tablets, or in liquid form such as a mouth spray or energy shot.

Example 10

Any of the foregoing examples is modified by combining the combined beta-hydroxybutyrate/acetoacetate composition with a dietetically or pharmaceutically acceptable carrier.

Example 11

Any of the foregoing examples is modified by combining the combined beta-hydroxybutyrate/acetoacetate composition with one or more medium chain triglycerides and/or one or more medium chain fatty acids and/or one or more mono- or diglycerides of medium chain fatty acids.

Example 12

Any of the foregoing examples is modified by combining the combined beta-hydroxybutyrate/acetoacetate composition with one or more short chain triglycerides and/or one or more short chain fatty acids and/or one or more mono- or diglycerides of short chain fatty acids.

Example 13

Any of the foregoing examples is modified by combining the combined beta-hydroxybutyrate/acetoacetate composition with one or more long chain triglycerides and/or one or more long chain fatty acids and/or one or more mono- or diglycerides of long chain fatty acids.

Example 14

Any of the foregoing examples is modified by combining the combined beta-hydroxybutyrate/acetoacetate composition with one or more supplements, such as vitamin $D_3$, vitamins, minerals, and others known in the art.

Example 15

Any of the foregoing examples is modified by combining the combined beta-hydroxybutyrate/acetoacetate composition with NAD+.

Example 16

Any of the foregoing examples is modified by combining the combined beta-hydroxybutyrate/acetoacetate composition with caffeine and/or other stimulant(s) known in the art.

Example 17

Any of the foregoing examples is modified by combining two or more different carrier component forms to form a stacked composition.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A composition for administering ketone bodies to a subject, comprising:
   one or more beta-hydroxybutyrate salts;
   one or more acetoacetate salts;
   beta-hydroxybutyrate free acid; and
   optionally acetoacetate free acid.

2. The composition of claim 1, wherein the composition comprises:
   about 2% to about 98% on a combined molar basis of the one or more beta-hydroxybutyrate salts and the one or more acetoacetate salts; and
   about 2% to about 98% on a combined molar basis of the beta-hydroxybutyrate free acid and optionally the acetoacetate free acid.

3. The composition of claim 1, wherein the composition comprises:
   about 55% to about 95% by combined weight of the one or more beta-hydroxybutyrate salts and the beta-hydroxybutyrate free acid; and
   about 5% to about 45% by total weight of the one or more acetoacetate salts and optionally the acetoacetate free acid.

4. The composition of claim 1, wherein the one or more beta-hydroxybutyrate salts are selected from the group consisting of sodium beta-hydroxybutyrate, potassium beta-hydroxybutyrate, magnesium beta-hydroxybutyrate, calcium beta-hydroxybutyrate, lithium beta-hydroxybutyrate, and amino acid beta-hydroxybutyrate.

5. The composition of claim 1, wherein the one or more acetoacetate salts are selected from the group consisting of sodium acetoacetate, potassium acetoacetate, magnesium acetoacetate, calcium acetoacetate, lithium acetoacetate, and amino acid acetoacetate.

6. The composition of claim 1, further comprising at least one ketone body ester selected from the group consisting of beta-hydroxybutyrate esters and acetoacetate esters.

7. The composition of claim 6, wherein the ketone body ester comprises at least one of a mono-ester of ethanol, a mono-ester of 1-propanol, a mono-ester of 1,3-propanediol, a di-ester of 1,3-propanediol, a mono-ester of 1,3-butanediol, a di-ester of 1,3-butanediol, a mono-ester of glycerin, a di-ester of glycerin, or a tri-ester of glycerin.

8. The composition of claim 1, wherein the composition is a beverage.

9. The composition of claim 1, wherein the composition is a mouth spray or energy shot.

10. The composition of claim 1, wherein the composition is a powder, liquid, gel, suspension, tablet, capsule, food product, food additive, beverage additive, or food supplement.

11. The composition of claim 1, wherein the composition is free of medium chain fatty acids.

12. A kit for administering ketone bodies to a subject, comprising:
    a composition comprising one or more beta-hydroxybutyrate salts, one or more acetoacetate salts, beta-hydroxybutyrate free acid, and optionally acetoacetate free acid,
    a container in which the composition is placed, wherein the container is one or more of a carton, a box, a can, a jar, a bag, a pouch, a jug, or a keg; and
    a measuring device configured to hold therein a unit dose, or fraction thereof, of the composition, wherein a unit dose of the composition contains about 0.5 g to about 50 g of combined beta-hydroxybutyrate and acetoacetate salts, wherein the measuring device is one or more of a cup, a scoop, a syringe, a spoon, or a spatula.

13. The kit of claim 12, wherein the composition comprises about 2% to about 98% on a combined molar basis of the one or more beta-hydroxybutyrate salts and the one or more acetoacetate salts and about 2% to about 98% on a combined molar basis of the beta-hydroxybutyrate free acid and optionally the acetoacetate free acid.

14. The kit of claim 12, wherein:
    the one or more beta-hydroxybutyrate salts are selected from the group consisting of sodium beta-hydroxybutyrate, potassium beta-hydroxybutyrate, magnesium beta-hydroxybutyrate, calcium beta-hydroxybutyrate, lithium beta-hydroxybutyrate, transition metal beta-hydroxybutyrate, and amino acid beta-hydroxybutyrate; and
    the one or more acetoacetate salts are selected from the group consisting of sodium acetoacetate, potassium acetoacetate, magnesium acetoacetate, calcium acetoacetate, lithium acetoacetate, transition metal acetoacetate, and amino acid acetoacetate.

15. The kit of claim 12, wherein the composition is free of medium chain fatty acids.

16. A composition for administering ketone bodies to a subject, the composition comprising:
    one or more beta-hydroxybutyrate salts selected from the group consisting of alkali metal beta-hydroxybutyrate salts and alkaline earth metal beta-hydroxybutyrate salts;
    one or more acetoacetate salts selected from the group consisting of alkali metal acetoacetate salts and alkaline earth metal acetoacetate salts;
    beta-hydroxybutyrate free acid; and
    optionally acetoacetate free acid,
    wherein the composition is free of medium chain triglycerides.

17. The composition of claim 16, further comprising one or more ketone body esters selected from the group consisting of beta-hydroxybutyrate esters and acetoacetate esters.

18. The composition of claim 16, wherein the composition comprises a plurality of beta-hydroxybutyrate salts selected from the group consisting of sodium beta-hydroxybutyrate, potassium beta-hydroxybutyrate, magnesium beta-hydroxybutyrate, and calcium beta-hydroxybutyrate.

19. The composition of claim 16, wherein the composition comprises a plurality of acetoacetate salts selected from the group consisting of sodium acetoacetate, potassium acetoacetate, magnesium acetoacetate, and calcium acetoacetate.

20. The composition of claim 16, wherein the composition comprises:
    about 2% to about 98% on a combined molar basis of the one or more beta-hydroxybutyrate salts and the one or more acetoacetate salts; and
    about 2% to about 98% on a combined molar basis of the beta-hydroxybutyrate free acid and optionally the acetoacetate free acid.

* * * * *